(12) United States Patent
Masuda et al.

(10) Patent No.: US 10,281,267 B2
(45) Date of Patent: May 7, 2019

(54) METHOD FOR EVALUATING FLOW OF SKIN, METHOD FOR EXAMINING SKIN GLOW IMPROVERS, AND SKIN GLOW IMPROVER

(71) Applicant: Shiseido Company, Ltd., Chuo-ku, Tokyo (JP)

(72) Inventors: Yuji Masuda, Yokohama (JP); Eiichiro Yagi, Yokohama (JP); Tomohiro Kuwahara, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 15/525,133

(22) PCT Filed: Nov. 10, 2015

(86) PCT No.: PCT/JP2015/081615
§ 371 (c)(1),
(2) Date: May 8, 2017

(87) PCT Pub. No.: WO2016/076313
PCT Pub. Date: May 19, 2016

(65) Prior Publication Data
US 2017/0336199 A1    Nov. 23, 2017

(30) Foreign Application Priority Data
Nov. 10, 2014  (JP) ................ 2014-228494

(51) Int. Cl.
*G01B 11/30*     (2006.01)
*A61K 8/368*     (2006.01)
(Continued)

(52) U.S. Cl.
CPC ............ *G01B 11/30* (2013.01); *A61B 5/00* (2013.01); *A61B 5/0059* (2013.01); *A61B 5/107* (2013.01);
(Continued)

(58) Field of Classification Search
CPC ......... G01B 11/30; A61B 5/00; A61B 5/0059; A61B 5/107; A61B 5/441; A61K 8/368;
(Continued)

(56) References Cited

U.S. PATENT DOCUMENTS

| | | | |
|---|---|---|---|
| 2003/0134264 A1 | 7/2003 | Maeda et al. | |
| 2008/0194928 A1* | 8/2008 | Bandic | G16H 15/00 600/306 |

(Continued)

FOREIGN PATENT DOCUMENTS

| | | |
|---|---|---|
| JP | 06-040886 A | 2/1994 |
| JP | 2000-063255 A | 2/2000 |

(Continued)

*Primary Examiner* — Hina F Ayub
(74) *Attorney, Agent, or Firm* — Foley & Lardner LLP

(57) ABSTRACT

Provided are an evaluation method for objectively evaluating the glow of the skin, a skin glow improver, and a method for examining skin glow improvers. This method for evaluating the glow of the skin comprises assessing the specular reflectance and diffuse reflectance of skin after polarized light is applied to the surface of the skin, and determining that glow is present in the skin when prescribed conditions are satisfied. A skin glow improver is provided by combining an alkali metal salt of alkoxysalicylic acid and trimethylglycine. This method for examining skin glow improvers makes it possible, using a significant decrease in surface roughness as an indicator, to examine samples capable of improving the specular reflectance of the skin.

5 Claims, 22 Drawing Sheets

(51) Int. Cl.
  *A61K 8/44*     (2006.01)
  *A61B 5/00*     (2006.01)
  *A61Q 19/00*    (2006.01)
  *A61B 5/107*    (2006.01)
  *G01N 21/21*    (2006.01)
  *G01N 21/57*    (2006.01)

(52) U.S. Cl.
  CPC .............. *A61B 5/441* (2013.01); *A61K 8/368* (2013.01); *A61K 8/44* (2013.01); *A61Q 19/00* (2013.01); *G01N 21/21* (2013.01); *G01N 21/57* (2013.01)

(58) Field of Classification Search
  CPC .......... A61K 8/44; A61Q 19/00; G01N 21/21; G01N 21/57
  USPC ........................................................ 356/369
  See application file for complete search history.

(56)        References Cited

U.S. PATENT DOCUMENTS

2009/0081142  A1   3/2009   Omura et al.
2010/0010241  A1   1/2010   Omura et al.
2011/0196616  A1*  8/2011   Gunn ..................... A61B 5/441
                                                         702/19
2013/0079410  A1   3/2013   Omura et al.
2013/0216247  A1*  8/2013   Oba ................... G03G 15/5029
                                                         399/45
2014/0186281  A1   7/2014   Furukawara et al.

FOREIGN PATENT DOCUMENTS

JP    2003-252718 A    9/2003
JP    2004-215991 A    8/2004
JP    2005-239623 A    9/2005
JP    2005-320263 A    11/2005
JP    2006-298834 A    11/2006
JP    2007-145721 A    6/2007
JP    2008-156326 A    7/2008
JP    2008-230995 A    10/2008
JP    2009-102281 A    5/2009
JP    2012-006902 A    1/2012
JP    2012-020988 A    2/2012
JP    2013-040114 A    2/2013
JP    2013-189396 A    9/2013

* cited by examiner

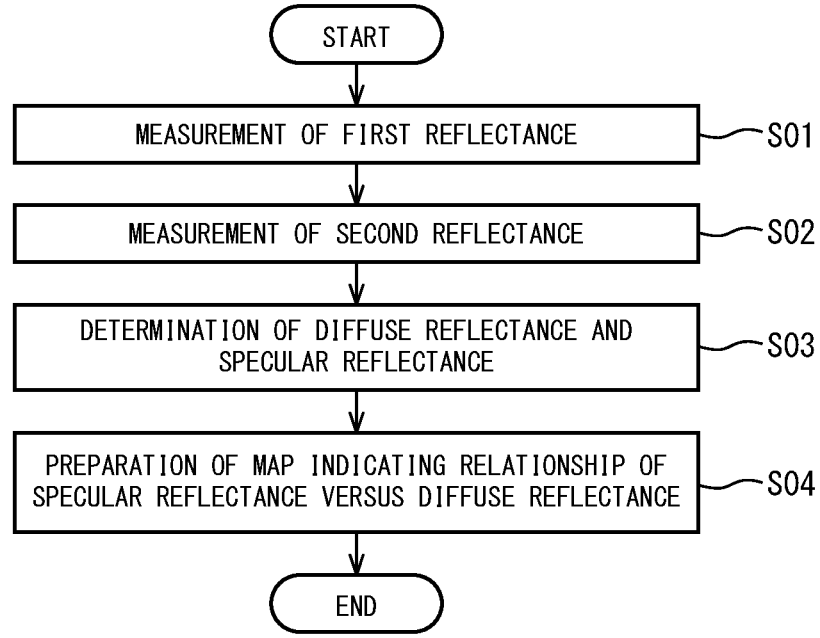
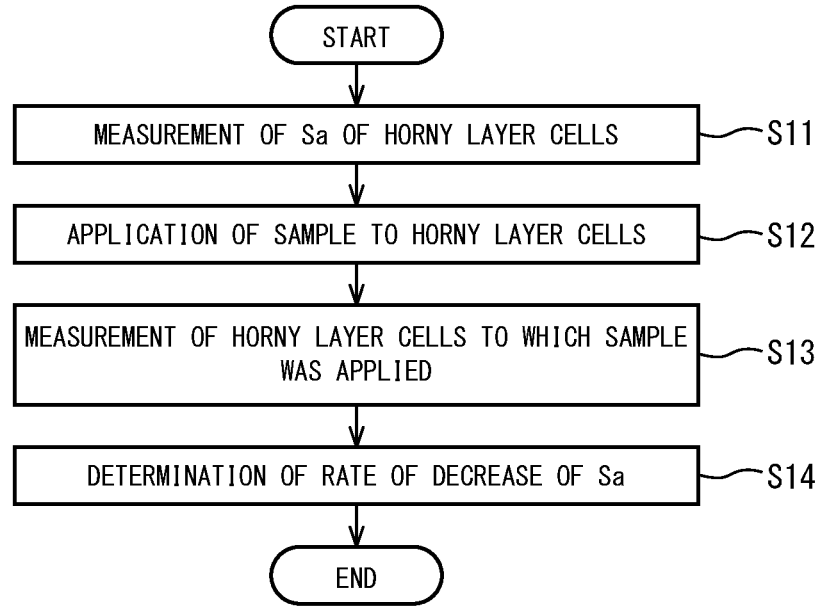

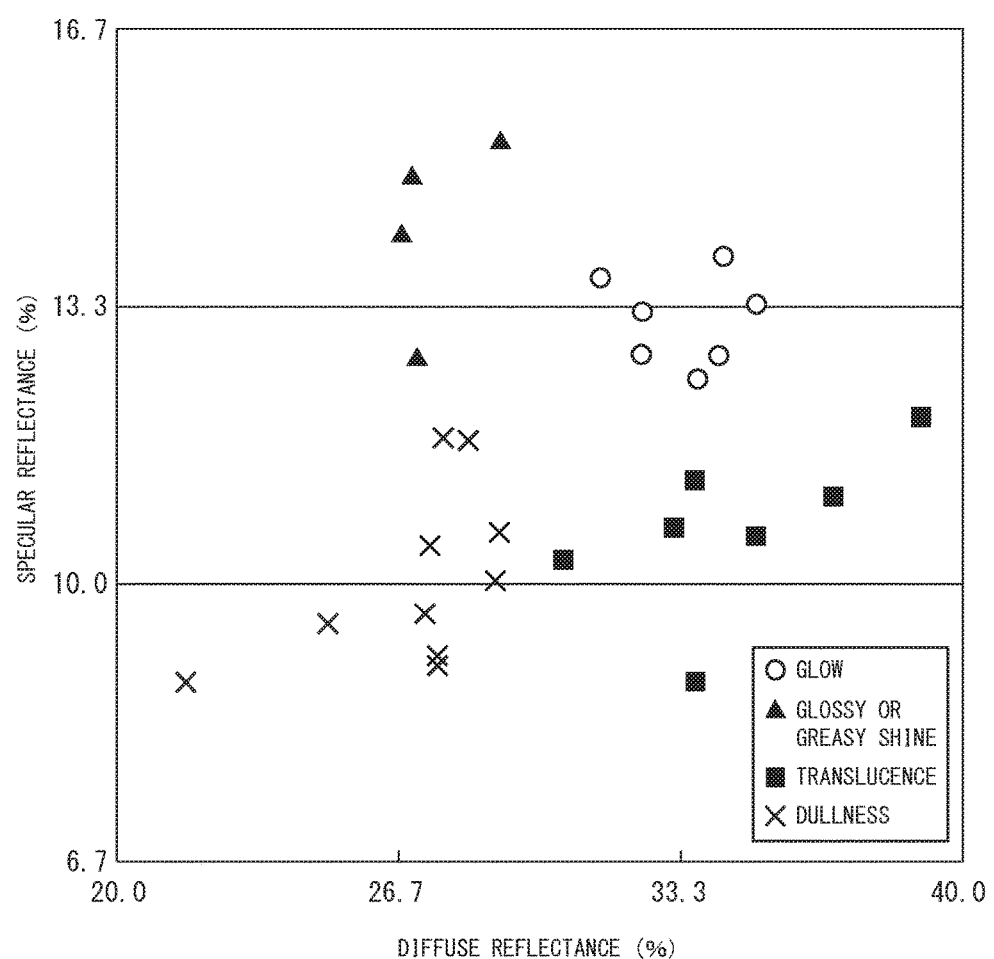

n=5, mean+s.d.

METHOD FOR EVALUATING FLOW OF SKIN, METHOD FOR EXAMINING SKIN GLOW IMPROVERS, AND SKIN GLOW IMPROVER

CROSS-REFERENCE TO RELATED APPLICATIONS

This application is a National Stage application of PCT/JP2015/081615, filed Nov. 10, 2015, which claims priority from Japanese application JP 2014-228494, filed Nov. 10, 2014.

TECHNICAL FIELD

The present invention relates to a method for evaluating the glow of skin, a method for screening a skin glow improver and a skin glow improver.

BACKGROUND ART

Translucency has conventionally been known to serve as an indicator of the appearance of skin. Translucency has been determined by sensory evaluations which are conducted by a beauty technician visually, wherein an external skin preparation is applied to the skin as necessary.

However, in addition to requiring many years of experience in order to evaluate skin translucency accurately, even if skin translucency was evaluated by a technician having ample experience, it was difficult to completely eliminate variations between evaluations.

For example, a conventional method for evaluating skin translucency is known that is based on the total reflectance of two types of reflected light consisting of an S-polarized light component and a P-polarized light component obtained by irradiating P-polarized light to the surface of skin and receiving reflected light in the form of an S-polarized polarized light component, and irradiating S-polarized light to the surface of skin and receiving reflected light in the form of a P-polarized light component (see, for example, PLT 1: Japanese Unexamined Patent Publication No. 2004-215991).

On the other hand, external skin preparations containing one or more an alkoxysalicylic acid and/or salt thereof are known as examples of external skin preparations having a skin whitening effect (see, for example, PLT 2: Japanese Unexamined Patent Publication No. H6-40886).

CITATION LIST

Patent Literature

PLT 1: Japanese Unexamined Patent Publication No. 2004-215991

PLT 2: Japanese Unexamined Patent Publication No. H6-40886

PLT 3: Japanese Unexamined Patent Publication No. 2013-189396

PLT 4: Japanese Unexamined Patent Publication No. 2013-40114

PLT 5: Japanese Unexamined Patent Publication No. 2000-63255

PLT 6: Japanese Unexamined Patent Publication No. 2012-6902

SUMMARY OF INVENTION

Technical Problem

However, there has been no method available for objectively evaluating skin glow. Consequently, there is a desire to develop a method for evaluating skin glow. In addition, there is also a desire to develop a compound or composition capable of improving skin glow, namely a skin glow improver, and a method for screening such skin glow improvers.

Taking into consideration the problem which the prior art may cause, one aspect of the present invention is directed to evaluating the glow of skin, a skin glow improver, and a method for examining skin glow improvers.

Solution to Problem

One aspect of the present invention is a method for evaluating the glow of skin, comprising: a step for measuring a first reflectance by irradiating polarized light to the surface of skin followed by receiving reflected light polarized in a direction parallel to the direction of polarization of the irradiated polarized light, a step for measuring a second reflectance by applying the polarized light to the surface of the skin followed by receiving reflected light in a direction perpendicular to the direction of polarization of the irradiated polarized light, and a step for determining diffuse reflectance and specular reflectance from the first reflectance and the second reflectance; wherein, the skin is determined to have glow in the case the diffuse reflectance and the specular reflectance satisfy prescribed conditions.

One aspect of the present invention is a method for screening a skin glow improver, comprising: a step for measuring surface roughness of horny layer cells, a step for applying a test sample to the horny layer cells, and a step for measuring surface roughness of the horny layer cells to which the test sample has been applied; wherein, the test sample is judged to be able to improve specular reflectance of the skin in the case surface roughness of the horny layer cells to which the test sample has been applied decreases significantly in comparison with surface roughness of the horny layer cells to which the test sample has not been applied.

One aspect of the present invention is a skin glow improver, comprising one or more medicinal agents selected from the group consisting of an alkaline metal salt of salicylic acid, an alkaline metal salt of an alkoxysalicylic acid and glycolic acid.

More specifically, the present invention relates to that indicated below.

[1] A skin glow improver, comprising an alkaline metal salt of an alkoxysalicylic acid and trimethylglycine.

[2] The skin glow improver described in [1], wherein the alkaline metal salt of an alkoxysalicylic acid is potassium 4-methoxysalicylate.

[3] The skin glow improver described in [2], comprising 0.5% to 3% of potassium 4-methoxysalicylate.

[4] The skin glow improver described in any of [1] to [3], comprising 2% to 10% of trimethylglycine.

[5] A method for screening a skin glow improver, comprising:
measuring surface roughness of horny layer cells,
applying a test sample to the horny layer cells, and
measuring surface roughness of the horny layer cells to which the test sample has been applied;
wherein the sample is determined to be able to improve specular reflectance of skin in the case surface roughness of the horny layer cells to which the test sample has been applied decreases significantly in comparison with surface roughness of the horny layer cells to which the test sample has not been applied.

[6] A method for evaluating the glow of skin, comprising:
measuring a first reflectance by irradiating polarized light to the surface of skin followed by receiving reflected light polarized in a direction parallel to the direction of polarization of the irradiated polarized light,
measuring a second reflectance by irradiating polarized light to the surface of the skin followed by receiving reflected light in a direction perpendicular to the direction of polarization of the irradiated polarized light, and
determining diffuse reflectance and specular reflectance from the first reflectance and the second reflectance;
wherein the skin is determined to have glow in the case the diffuse reflectance and the specular reflectance satisfy prescribed conditions.

[7] The method for evaluating skin glow described in [6], further comprising a step for applying a sample to skin before measuring the first reflectance and the second reflectance.

[8] Use of an alkaline metal salt of an alkoxysalicylic acid and trimethylglycine for the production of a skin glow improver and specular reflectance enhancer.

[9] The use described in [8], wherein the alkaline metal salt of an alkoxysalicylic acid is potassium 4-methoxysalicylate.

[10] The use described in [9], wherein 0.5% to 3% of potassium 4-methoxysalicylate is used.

[11] The use described in any of [8] to [10], wherein 2% to 10% of trimethylglycine is used.

[12] A method for improving skin glow, a method for enhancing specular reflectance or a cosmetic method, comprising the application of an alkaline metal salt of an alkoxysalicylic acid and trimethylglycine.

[13] The method described in [12], wherein the alkaline metal salt of an alkoxysalicylic acid is potassium 4-methoxysalicylate.

[14] The method described in [13], wherein 0.5% to 3% of potassium 4-methoxysalicylate is used.

[15] The method described in any of [8] to [10], wherein 2% to 10% of trimethylglycine is used.

Advantageous Effects of Invention

According to one aspect of the present invention, a method for evaluating the glow of skin, a skin glow improver and a method for screening a skin glow improver can be provided.

BRIEF DESCRIPTION OF THE DRAWINGS

FIG. 1 is a flow chart indicating an example of the method for evaluating the glow of skin in the present embodiment.
FIG. 2 is a flow chart indicating an example of the method for screening a skin specular reflectance improver in the present embodiment.
FIG. 3 is a map indicating the relationship of specular reflectance versus diffuse reflectance in Example 1.

DESCRIPTION OF EMBODIMENTS

Figure 4:
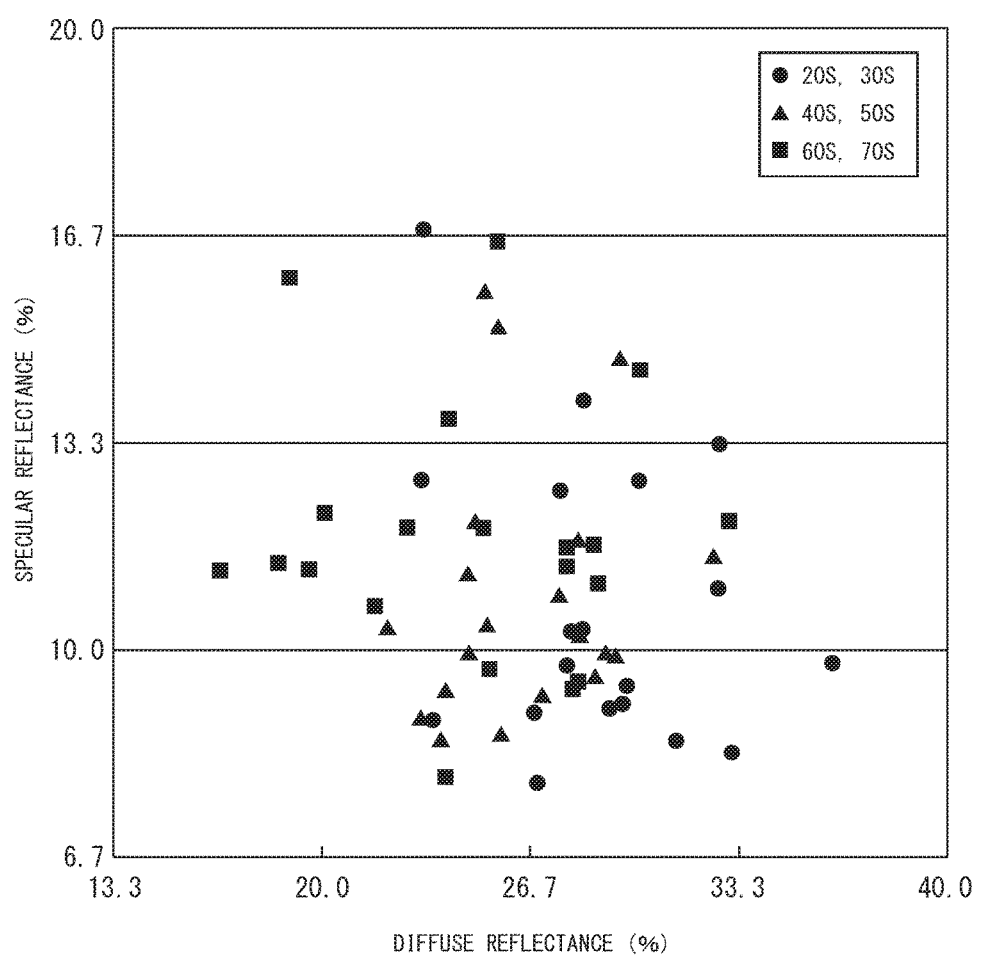
FIG. 4 is a map indicating the relationship of specular reflectance versus diffuse reflectance in Example 2.

The following provides an explanation of embodiments for carrying out the invention along with drawings.

Skin glow is one of the properties of skin that makes skin appear beautiful. Examples of properties of the skin surface that make skin appear beautiful include translucence and glow. Translucence is thought to have an effect on the color of skin. Diffuse reflectance of light by the skin is thought to contribute to translucence (Measurement of Skin Translucence and Evaluation of the Usefulness of Applicable Cosmetics, J. Soc. Cosmet. Chem. Japan, 2005, 39: 201-208), and translucence can be increased by increasing diffuse reflectance of light by the skin as a result of whitening. In addition to whitening, moisture retention and promotion of blood circulation also contribute to increased translucence. Although glow refers to the luster of skin, the aesthetically undesirable property of glossy or greasy shine is also related to luster, and since this makes it difficult to distinguish between them when evaluating skin, skin glow has yet to be evaluated properly. According to research conducted by the inventors of the present invention, it was found that skin glow can be realized by additionally increasing specular reflectance in skin having translucence resulting from an increase in diffuse reflectance (FIG. 3), and skin glow is therefore thought to involve both diffuse reflectance and spectral reflectance. The glow of skin can be represented by several parameters, and can be referred to as glow, luminous sheen, luster or sheen. Thus, the skin glow improver of the present invention can be said to be a luminous sheen or luster improver.

Light that is radiated onto skin is partially reflected resulting in reflected light. This reflected light can be broadly categorized as specular reflection and diffuse reflection. Specular reflection refers to light from one direction being reflected in another direction, and specular reflection in the skin refers to reflection generated mainly on the skin surface. Although specular reflection in the skin is thought to contribute to skin luster, properties of the skin relating to skin luster not only include glow, but also include a glossy or greasy shine. Although glow is a property that makes the skin appear beautiful, since a glossy or greasy shine is produced by secretion of large amounts of sebaceous matter, it is considered to be a property of skin that is aesthetically undesirable. Diffuse reflection refers to incoming light being reflected in various directions, and refers to reflection occurring within the skin. Diffuse reflection in the skin contributes to skin translucence, and skin having a low level of diffuse reflection gives a dull impression.

According to research conducted by the inventors of the present invention, while enhancement of only specular reflection results in a glossy or greasy shine, it was clearly determined that enhancement of specular reflection in translucent skin having a high degree of diffuse reflection could result in glow skin (FIG. 3). On the basis of these findings, the present invention relates to a method for evaluating the glow of skin using reflected light polarized in a direction parallel to the polarized direction of irradiated polarized light and reflected light polarized in a direction perpendicular to the polarized direction of irradiated polarized light as an indicator, when polarized light is irradiated onto the skin surface, as will be subsequently described.

<Method for Evaluating Glow of Skin>

The method for evaluating the glow of skin of the present invention comprises:

a step for irradiating polarized light to the surface of skin, a step for measuring reflected light polarized in a direction parallel to the direction of polarization of the irradiated polarized light (parallel reflected light) and reflected light polarized in a direction perpendicular to the direction of polarization (perpendicular reflected light), a step for calculating reflectance of the parallel reflected light and the perpendicular reflected light, and a step for determining the glow of skin based on parallel reflectance and perpendicular reflectance.

In the step for determining the glow of skin based on parallel reflectance and perpendicular reflectance, the glow of the skin can be determined based on a graph indicating the relationship between skin glow and the preliminarily determined parallel reflectance and perpendicular reflectance, or can be determined based on a predetermined threshold value. In still another aspect, the step for determining the glow of skin based on parallel reflectance and perpendicular reflectance may also include a step for calculating specular reflectance and diffuse reflectance from parallel reflectance and perpendicular reflectance. In this case, the glow of skin can be determined based on a graph indicating the relationship between skin glow and predetermined specular reflectance and diffuse reflectance, or can be determined based on a predetermined threshold value.

According to the present invention, the glow of skin, which conventionally was only able to be evaluated by a sensory evaluation relying on a visual evaluation by a beauty technician, can be evaluated objectively.

An explanation of the method for evaluating the glow of skin in a specific embodiment of the present invention is provided using FIG. 1.

First, after having irradiated polarized light to the skin surface, a first reflectance (parallel reflectance) is measured by receiving reflected light polarized in a direction parallel to the direction of polarization of the irradiated polarized light (S01).

In this connection, the direction parallel to the direction of polarization of the irradiated polarized light refers to the direction parallel to the direction of polarization in the case of the irradiated polarized light having been reflected on the surface of the skin without undergoing a change in the direction of polarization.

Next, after having irradiated polarized light to the skin surface, a second reflectance (perpendicular reflectance) is measured by receiving reflected light in a direction perpendicular to the direction of polarization of the irradiated polarized light (S02). Here, the surface of the skin to which the polarized light was irradiated and the polarized light applied to the surface of the skin are the same as in S01.

In this connection, the direction perpendicular to the direction of polarization of the irradiated polarized light refers to the direction perpendicular to the direction of polarization in the case of the irradiated polarized light having been reflected on the surface of the skin without undergoing a change in the direction of polarization.

At this time, there are no particular limitations on the order of S01 and S02.

Moreover, diffuse reflectance and specular reflectance are determined form the first reflectance and the second reflectance (S03).

Next, a map is prepared that indicates the relationship of the specular reflectance versus the diffuse reflectance determined in S03 (S04). Here, skin is determined to have glow in the case diffuse reflectance and specular reflectance satisfy prescribed conditions. At this time, evaluation criteria can be determined by determining the diffuse reflectance and specular reflectance of a plurality of preliminary subjects and evaluating the skin glow of the plurality of preliminary subjects by visual sensory evaluations performed by a beauty technician.

As an example thereof, skin is judged to have glow in the case diffuse reflectance is equal or greater than a prescribed value and specular reflectance is equal to or greater than a prescribed value. In this case, diffuse reflectance at which skin is judged to have glow is normally 25% or more and preferably 27% or more. In addition, specular reflectance at which skin is judged to have glow is normally 10% or more and preferably 12% or more.

Although there are no particular limitations on the site of the skin where total reflectance, first reflectance and second reflectance are measured, an example thereof is the cheeks (and particularly the area of the upper cheek directly below the corner of the eye (cheekbone)).

Furthermore, the first reflectance and the second reflectance can be measured using a known method (see, for example, PTL 1: Japanese Unexamined Patent Publication No. 2004-215991).

The method for evaluating the glow of skin in the present embodiment may also further comprise a step for applying a sample to the skin prior to measuring the first reflectance and the second reflectance. In this case, skin glow improvers can be screened by determining diffuse reflectance and spectral reflectance before and after applying the sample to the skin.

<Method for Calculating Diffuse Reflectance and Specular Reflectance>

Diffuse reflectance can be calculated from formula (1) and specular reflectance can be calculated from formula (2) by defining first reflectance (parallel reflectance) and second reflectance (perpendicular reflectance) as $x_1$ (%) and $x_2$ (%), respectively.

$$2x_2 \quad (1)$$

$$x_1 - x_2 \quad (2)$$

Next, an explanation is provided of the method for screening a skin glow improver. Here, an explanation is provided of a method for screening a skin glow improver that is simpler than methods for screening skin glow improvers by using the method for evaluating the glow of skin of FIG. 1.

<Method for Screening a Skin Glow Improver>

As was previously described, in order to improve the glow of skin, it is necessary to enhance the diffuse reflectance and specular reflectance of skin. Here, skin diffuse reflectance is typically known to be high in skin having a smooth texture, low levels of melanin and hemoglobin, and high horny layer moisture content. In addition, application of cosmetics incorporating a whitening agent (such as albumin or ethyl vitamin C), circulation promoter (such as vitamin E acetate) or moisturizer (such as glycerin) are known to increase the diffuse reflectance of skin (see, for example, J. Soc. Cosmet. Chem. Jpn., 39(3), 201-208 (2005)).

However, with respect to specular reflectance, it has not yet known as to what types of properties of the skin are associated with this parameter, and it has not yet known as to a method for improving specular reflectance of the skin.

Therefore, in order to screen a skin glow improver, it is necessary to screen compounds or compositions that improve specular reflectance of skin, namely a skin specular reflectance improver.

Figure 7:
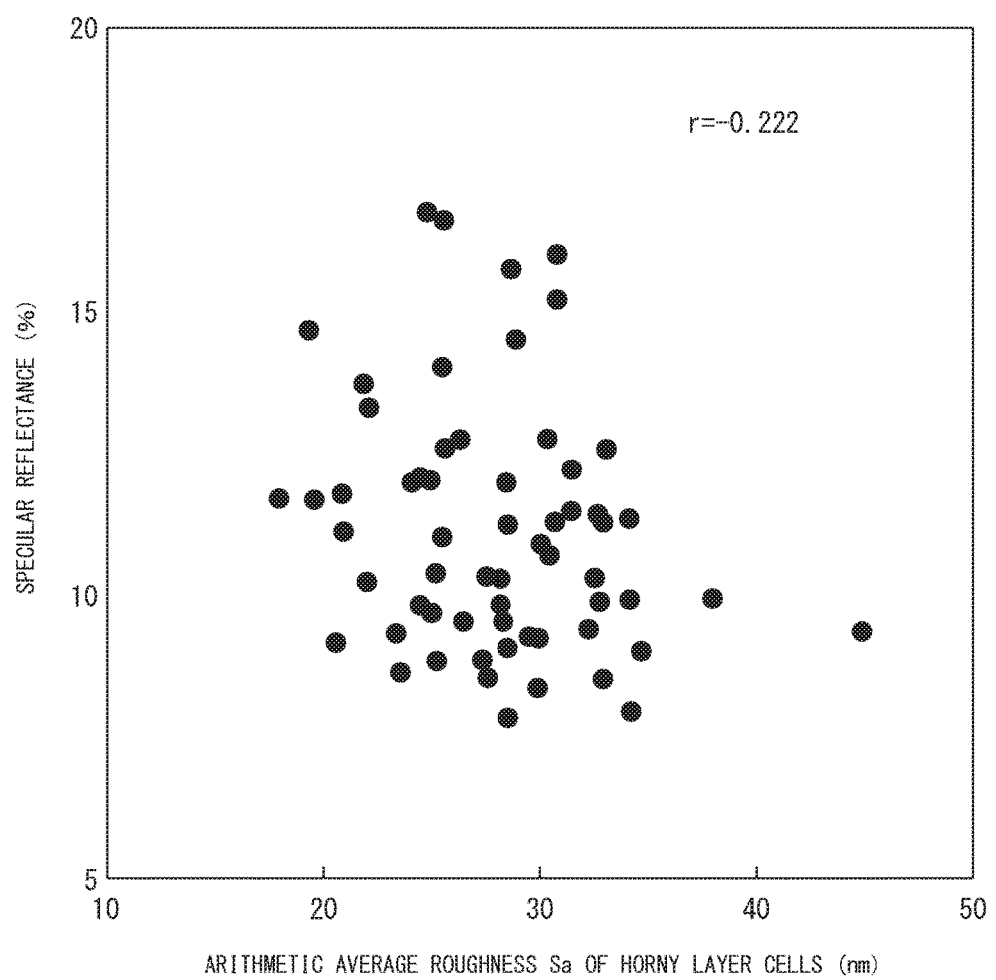
FIG. 7 is a map indicating the relationship of specular reflectance versus arithmetic average roughness (Sa) of horny layer cells in Example 4.

According to research conducted by the inventors of the present invention, decreasing the surface roughness of skin was found to be effective for enhancing specular reflection (FIG. 7). The surface roughness of skin as referred to in the present description does not refer to surface irregularities represented by skin depressions or protrusions, but rather refers to surface irregularities of horny layer cells present on smaller skin protrusions. Without intending to be limited by a particular theory, specular reflectance is thought to increase by a reduction in diffuse reflection of incoming light due to smoothening of surface irregularities of protruding portions of the skin. Thus, the action of smoothing the horny layer can be also said to be an action that increases specular reflectance, and horny layer smoothing agents can also be said to be specular reflectance enhancers.

The surface roughness of skin can be determined by measuring the surface of horny layer cells sampled with a strip of adhesive tape and the like using a microscope such as an atomic force microscope. Surface roughness can be calculated in terms of arithmetic average roughness (Sa) as defined in ISO25178 by acquiring 3D-scanned images captured using an atomic force microscope, correcting the inclination of the 3D shape by subtracting those images applicable to a Gaussian filter having a half width of 2 μm, displaying the images, and calculating the average of absolute values of the Z axis for each XY coordinate.

The following provides an explanation of the method for screening a skin specular reflectance improver of the present embodiment using FIG. 2.

First, the arithmetic average roughness (Sa) of horny layer cells is measured (S11). Next, a sample is applied to the horny layer cells (S12). Then, the arithmetic average roughness (Sa) of the horny layer cells to which the sample has been applied is measured (S13). Next, the rate of decrease of the arithmetic average roughness (Sa) of the horny layer cells to which the sample was applied is determined relative to the arithmetic average roughness of the horny layer cells to which the sample was not applied (S14). Here, the sample is judged to be able to improve the specular reflectance of skin in the case the arithmetic average roughness (Sa) of the horny layer cells to which the sample was applied significantly decreases relative to the arithmetic average roughness (Sa) of the horny layer cells to which the sample was not applied.

Furthermore, although arithmetic average roughness (Sa) of horny layer cells was used as an indicator for screening a skin specular reflectance improver in the present embodiment, there are no particular limitations thereon, as long as surface roughness of horny layer cells is used for the indicator. As a result of carrying out screening using the method for screening a skin specular reflectance improver of the present invention, the medicinal agent indicated below could be selected as a medicinal agent capable of improving specular reflectance. The action of improving glow can be demonstrated in the case of using a specular reflectance improver together with a medicinal agent having an action that improves translucence, in the case the specular reflectance improver per se has the effect of improving translucence, or in the case of using on a subject already having sufficiently translucent skin. Thus, a specular reflectance improver can also be referred to as a skin glow improver.

<Skin Glow Improver>

The skin glow improver comprises, for example, one or more types of medicinal agents selected from the group consisting of an alkaline metal salt of salicylic acid, an alkaline metal salt of an alkoxysalicylic acid and glycolic acid. Examples of alkaline metal salts include sodium salt, potassium salt and lithium salt.

The alkaline metal salt of salicylic acid includes, but is not limited to, sodium salicylate (sodium 2-hydroxybenzoate).

The alkaline metal salt of an alkoxysalicylic acid includes, but is not limited to, potassium 4-methoxysalicylate (2-hydroxy-4-methoxybenzoate). 4-methoxysalicylate is a cosmetic component known to demonstrate cuticle exfoliating action, melanin formation preventing action and turnover normalizing action, and is incorporated in cosmetics claiming primarily whitening action (PTL 3: Japanese Unexamined Patent Publication No. 2013-189396 and PTL 4: Japanese Unexamined Patent Publication No. 2013-40114). Although whitening action contributes to improvement of skin translucence by enhancing diffuse reflection, the specular reflectance improving action and glow improving action of potassium 4-methoxysalicylate were previously not known.

Although the incorporated amount of an alkaline metal salt of alkoxysalicylic acid can be selected arbitrarily, it can be incorporated in a cosmetic, for example, at a concentration of 0.5% by weight to 5% by weight. It is preferably incorporated at 1% by weight or more from the viewpoint of demonstrating glow improving action. On the other hand, since it is an effective medicinal agent, the incorporated amount thereof is preferably reduced provided the glow improving action thereof is demonstrated, and is preferably incorporated at 3% by weight or less. From the viewpoint of reducing the incorporated amount while demonstrating a glow improving action, the alkaline metal salt of an alkoxysalicylic acid is preferably incorporated at 1% by weight to 3% by weight, and for example, at 1% by weight, 1.5% by weight, 2% by weight, 2.5% by weight or 3% by weight.

Figure 9:
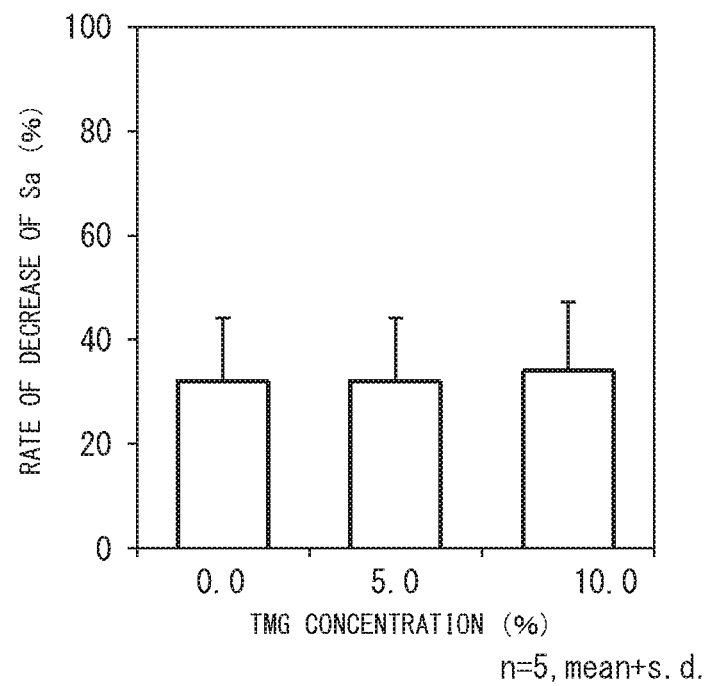
FIG. 9 indicates the rate of change of arithmetic average roughness (Sa) of horny layer cells after having added trimethylglycine (TMG) while changing the concentration thereof.
Figure 10:
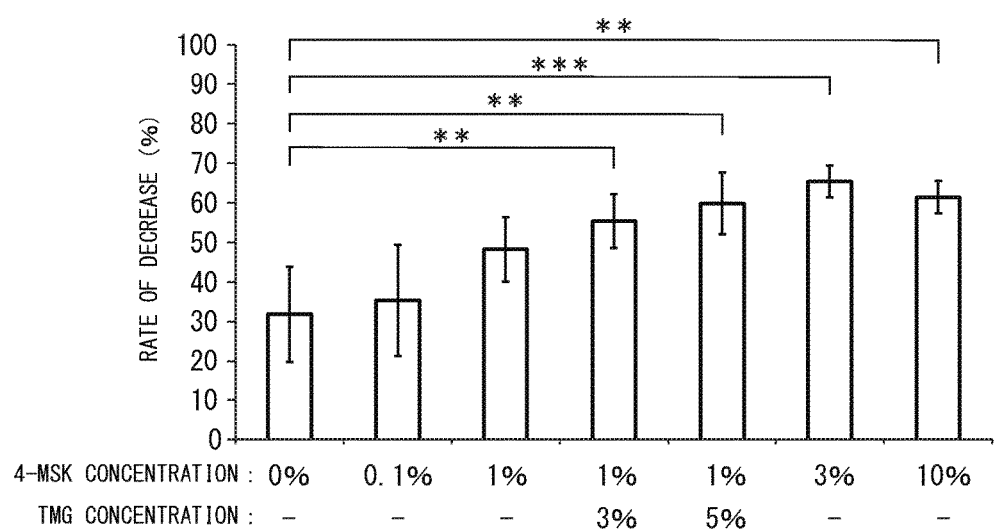
FIG. 10 indicates the rate of change of arithmetic average roughness (Sa) of horny layer cells after having added potassium 4-methoxysalicylate (4MSK) alone and combining potassium 4-methoxysalicylate (4-MSK) and trimethylglycine (TMG) while changing the concentrations thereof.

The skin glow improver may also further contain trimethyl glycine. As a result, the glow of skin can be further improved. Trimethylglycine is frequently incorporated in cosmetics as a moisturizer (PTL 5: Japanese Unexamined Patent Publication No. 2000-63255 and PTL 6: Japanese Unexamined Patent Publication No. 2012-6902). On the other hand, according to tests conducted by the inventors of the present invention, trimethylglycine does not have the effect of smoothing the horny layer or improving skin glow (FIG. 9). When the inventors of the present invention incorporated an alkaline metal salt of an alkoxysalicylic acid in the form of potassium 4-methoxysalicylate with trimethylglycine, synergistic effects were surprisingly observed with respect to horny layer smoothing effects (FIG. 10). Since potassium 4-methoxysalicylate is an expensive agent, it is imperative to reduce the amount used while maintaining glow improving action.

The incorporated amount of trimethylglycine can be arbitrarily selected provided synergistic action is demonstrated with respect to the glow improving action of an alkaline metal salt of an alkoxysalicylic acid, and can be incorporated in a cosmetic, for example, at a concentration of 1% by weight to 10% by weight. From the viewpoint of demonstrating a synergistic effect with the alkaline metal salt of an alkoxysalicylic acid with respect to the glow improving action thereof, trimethylglycine is preferably incorporated at 2% by weight or more, more preferably at 2.5% by weight or more, even more preferably at 3% by weight or more, and still more preferably at 5% by weight or more. Trimethylglycine is preferably incorporated at 8% by weight or less and more preferably at 6% by weight or less from the viewpoints of stability and usability.

The present invention also relates to use of one or more of agents selected from the group consisting of an alkaline metal salt of salicylic acid, an alkaline metal salt of an alkoxysalicylic acid and glycolic acid for the production of a skin glow improver or specular reflectance enhancer. In another aspect thereof, the present invention relates to use of one or more agents selected from the group consisting of an alkaline metal salt of salicylic acid, an alkaline metal salt of an alkoxysalicylic acid and glycolic acid, and trimethylglycine for the production of a skin glow improver or specular reflectance enhancer. The specific agents used and the concentrations thereof are as previously described.

In one aspect of the present invention, the present invention relates to a method for improving the glow of skin or enhancing the specular reflectance thereof, comprising application of one or more agents selected from the group consisting of an alkaline metal salt of salicylic acid, an alkaline metal salt of an alkoxysalicylic acid and glycolic acid. This method may further comprise the application of trimethylglycine. Subjects to which this method is applied may be arbitrary subjects such as subjects desiring to improve skin glow or enhance specular reflectance, and applicable subjects include subjects having skin problems such as dull skin or a glossy or greasy shine and subjects having translucent skin. The specific agents used and the concentrations thereof are as previously described. Although these agents can be applied using an arbitrary method and can be applied percutaneously, orally or enterally, percutaneous application by application to the skin is particularly preferable.

In another mode of the present invention, the present invention relates to a cosmetic method comprising the application of one or more agents selected from the group consisting of an alkaline metal salt of salicylic acid, an alkaline metal salt of an alkoxysalicylic acid and glycolic acid. This method may further comprise the application of trimethylglycine. Subjects to which this method is applied may be arbitrary subjects such as subjects desiring to improve skin glow or enhance specular reflectance, and applicable subjects include subjects having skin problems such as dull skin or a glossy or greasy shine and subjects having translucent skin. The specific agents used and the concentrations thereof are as previously described.

The skin glow improver includes, but is not limited to, skin lotions, milky lotions, beauty essences and creams, and the skin glow improver may be incorporated in these cosmetics. In addition, the skin glow improver can also be incorporated in pharmaceuticals or quasi-drugs, and can be incorporated in external skin preparations in particular. Medicinal agents commonly added to these cosmetics can also be contained, examples of which include moisturizers, whitening agents, antioxidants, oily components, ultraviolet absorbers, surfactants, thickeners, alcohols, colorants, fragrances, water, solvents, antiseptics, preservatives, pH adjusters, gelling agents and other active ingredients.

All documents mentioned in the present description are incorporated in the present description in their entirety by reference.

Examples of the present invention indicated below are provided for exemplary purposes only, and do not limit the technical scope of the present invention. The technical scope of the present invention is only limited by the description of the claims. The present invention can be modified, such as by adding, deleting or substituting constituents of the present invention, on the condition that such modification does not deviate from the gist of the present invention.

EXAMPLES

[Example 1] Evaluation of Skin Glow

The diffuse reflectance and specular reflectance of the cheeks of 28 subjects to which nothing had been applied were determined for cheeks presenting with glow, glossy or greasy shine, translucence and dullness using a skin gloss measuring device (Samba Face, Bossa Nova Technologies LLC). At this time, a polarizing filter was respectively installed on the front of the irradiation light source and the front of the light receiving camera. Here, parallel polarization images and perpendicular polarization images were acquired by making the direction of polarization of the polarizing filter on the front of the light receiving camera to be parallel or perpendicular to the direction of polarization of the polarizing filter on the irradiation light source, and diffuse reflectance and specular reflectance were determined from formulas (1) and (2). In addition, classification of glow, glossy or greasy shine, translucence and dullness was determined by sensory evaluation based on visual evaluations performed by multiple beauty technicians.

Furthermore, the direction parallel (or perpendicular) to the direction of polarization of the polarizing filters refers to the direction parallel (or perpendicular) to the direction of polarization in the case polarized light that has passed through a polarizing filter is reflected by the surface of the skin without undergoing a change in the direction of polarization.

FIG. 3 indicates a plot of specular reflectance versus diffuse reflectance, and is shown together with the results of sensory evaluations performed on the subjects.

It can be understood from FIG. 3 that those cheeks having glow demonstrated diffuse reflectance of 30% or more and specular reflectance of 12% or more.

[Example 2] Evaluation of Skin Glow in Subjects According to Age

The diffuse reflectance and specular reflectance of the cheeks of 20 subjects each in their twenties, thirties, forties, fifties, sixties and seventies to which nothing had been applied were determined using a skin gloss measuring device (Samba Face, Bossa Nova Technologies LLC) in the same manner as Example 1.

FIG. 4 indicates a plot of specular reflectance versus diffuse reflectance along with the ages of the subjects.

[Example 3] Change in Skin Glow Attributable to Application of Cosmetics

[Preparation of Skin Lotion]
water (balance), Ethanol (5% by weight), glycerin (10% by weight), dipropylene glycol (10% by weight), polyoxyethylene (10) methyl glucoside (1% by weight), erythritol (1% by weight), trehalose (1% by weight), sodium hyaluronate (0.1% by weight), polyoxyethylene (14) polyoxypropylene (7) dimethyl ether (1% by weight), carboxyvinyl polymer (0.1% by weight), sodium hydroxide (as suitable), polyoxyethylene (60) hydrogenated castor oil (0.2% by weight), polyglyceryl diisostearate (0.1% by weight), diphenylsiloxy phenyl trimethicone (0.2% by weight), isostearyl alcohol (0.1% by weight), isostearic acid (0.1% by weight), trisodium edetate (as suitable), phenoxyethanol (as suitable), and fragrance (as suitable) were mixed to obtain a skin lotion.

[Preparation of Milky Lotion]
Water (balance) and ethanol (5% by weight), glycerin (4% by weight), dipropylene glycol (5% by weight), sodium hyaluronate (0.1% by weight), carboxyvinyl polymer (0.1% by weight), xanthan gum (0.1% by weight), sodium hydroxide (as suitable), isostearic acid (0.5% by weight), stearic acid (0.5% by weight), behenic acid (0.5% by weight), self-emulsifying glyceryl monostearate (1% by weight), polyoxyethylene-glycerin monostearate (1% by weight), behenyl alcohol (1% by weight), Vaseline (3% by weight), pentaerythritol tetra(2-ethylhexanoate) (5% by weight), olefin oligomer (3% by weight), diphenylsiloxy phenyl trimethicone (2% by weight), trisodium edetate (as suitable), sodium metaphosphate (as suitable), phenoxyethanol (as suitable), and fragrance (as suitable) were mixed to obtain a milky lotion.

Application of the skin lotion and milky lotion to the cheeks of the subjects appeared to further enhance glow due to the physicochemical action thereof.

Figure 5:
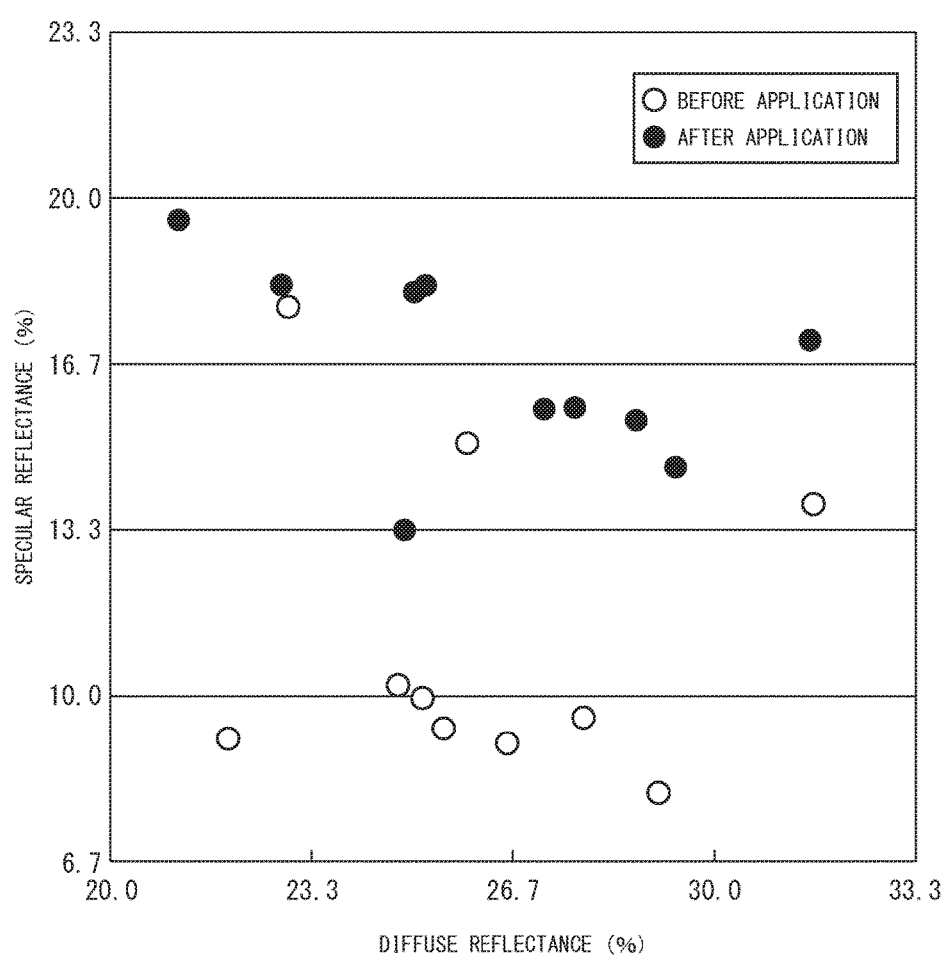
FIG. 5 is a map indicating the relationship of specular reflectance versus diffuse reflectance before and after applying a skin lotion and milky lotion in Example 3.

The diffuse reflectance and specular reflectance of the cheeks of 10 subjects to which nothing had been applied were determined using a skin gloss measuring device (Samba Face, Bossa Nova Technologies LLC) in the same manner as Example 1. Next, after applying the skin lotion and milky lotion to the cheeks of the subjects, diffuse reflectance and specular reflectance of the cheeks were determined in the same manner as described above. The relationship of specular reflectance versus diffuse reflectance before and after applying the skin lotion and milky lotion is indicated in FIG. 5. In addition, changes in specular reflectance before and after applying the skin lotion and milky lotions are indicated in FIG. 6.

Figure 6:
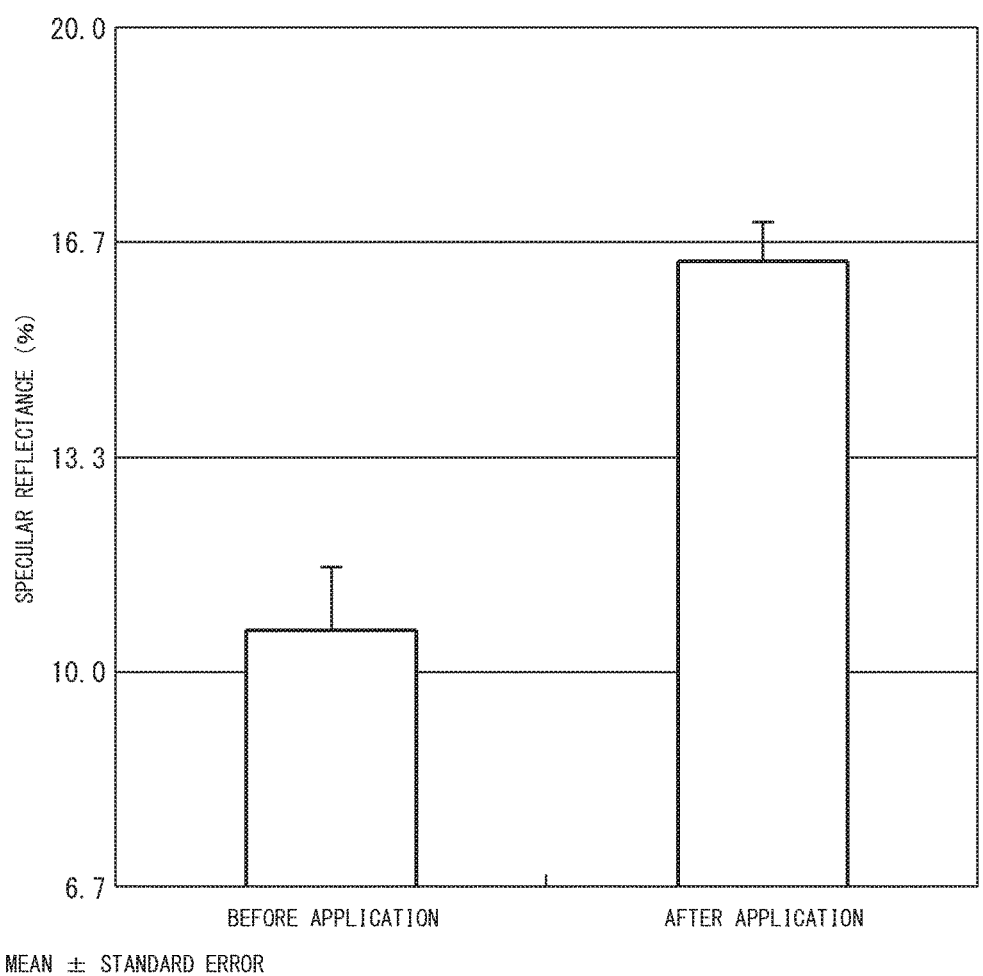
FIG. 6 is a graph indicating specular reflectance before and after applying a skin lotion and milky lotion in Example 3.

It can be understood from FIG. 6 that application of the skin lotion and milky lotion enhanced specular reflectance of the cheeks. Although changes in diffuse reflectance before and after application of the skin lotion and milky lotion were small, specular reflectance tended to increase following application. As a result of the skin lotion and milky lotion imparting moisture to the skin, surface irregularities in the surface of the horny layer were thought to have been temporarily smoothened, thereby resulting in an increase in specular reflectance. On the other hand, a study was conducted as indicated below on indicators that make it possible to screen medicinal agents capable of increasing specular reflectance in a state in which cosmetics such as skin lotion or milky lotion have not been applied.

[Example 4] Examination of Indicator Correlating with Skin Specular Reflectance

The diffuse reflectance and specular reflectance of the cheeks of 20 subjects each in their twenties, thirties, forties, fifties, sixties and seventies to which an external skin preparation has not been applied were determined using a skin gloss measuring device (Samba Face, Bossa Nova Technologies LLC).

On the other hand, horny layer cells were exfoliated from the cheeks of the subjects using adhesive strips (Post-It®, 3M Corp.). Next, double-sided adhesive tape was adhered to a slide glass and the exfoliated horny layer cells were transferred to the slide glass. Moreover, the arithmetic average roughness (Sa) of five horny layer cells was measured using an AFM attached to the Optelics H1200A 3CCD real color confocal microscope (Lasertec Corp.) followed by determination of the average value thereof.

FIG. 7 indicates the relationship of specular reflectance versus arithmetic average roughness (Sa) of the horny layer cells.

It can be understood from FIG. 7 that the correlation coefficient between arithmetic average roughness (Sa) of the horny layer cells and specular reflectance was observed to be −0.222, thus demonstrating a negative correlation. Namely, specular reflectance was determined to improve as a result of a decrease in the arithmetic average roughness (Sa) of horny layer cells. Therefore, skin specular reflectance improvers were screened using the arithmetic average roughness (Sa) of horny layer cells as an indicator.

[Example 5] Screening of Specular Reflectance Improvers

Horny layer cells were exfoliated from the cheeks of subjects using adhesive strips (Post-It®, 3M Corp.). Next, double-sided adhesive tape was adhered to a slide glass and the exfoliated horny layer cells were transferred to the slide glass. Moreover, the arithmetic average roughness (Sa) of five horny layer cells was measured using an AFM attached to the Optelics H1200A 3CCD real color confocal microscope (Lasertec Corp.) followed by determination of the average value thereof. Next, 100 µl of a candidate sample were dropped onto the horny layer cells followed by incubating for 30 minutes at 37° C. Moreover, arithmetic average roughness (Sa) of the aforementioned five horny layer cells was then measured in the same manner followed by determination of the average value thereof. The aforementioned sample was judged to be able to improve the specular reflectance of skin in the case the surface roughness of horny layer cells to which the aforementioned sample had been applied decreases significantly in comparison with the surface roughness of horny layer cells to which the candidate sample had not been applied.

As a result of screening candidate samples for nine types of cosmetic ingredients, potassium 4-methoxysalicylate (4-MSK), sodium salicylate and glycolic acid were determined to be specular reflectance improvers. Candidate samples obtained as a result of screening were further analyzed in the following formulations.

[Sample Preparation 1]

Candidate samples of potassium 4-methoxysalicylate (4-MSK) were prepared at concentrations of 0% by weight, 0.1% by weight, 1.0% by weight, 3.0% by weight and 10.0% by weight.

Figure 8:
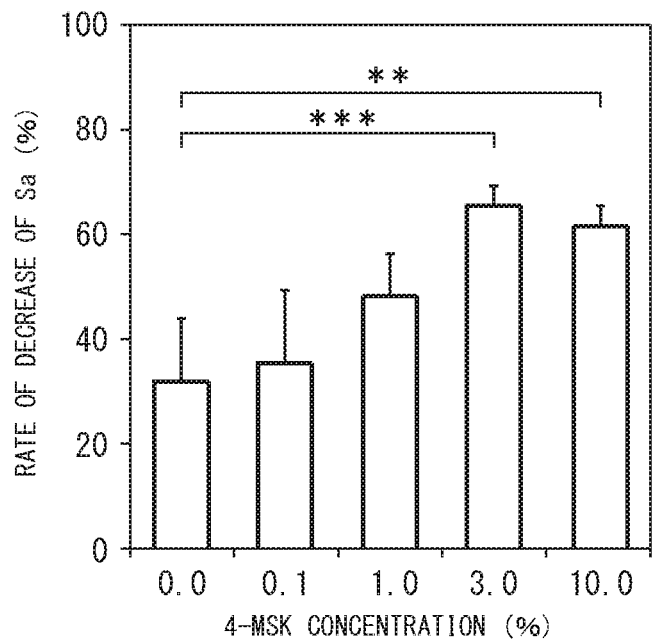
FIG. 8 indicates the rate of change of arithmetic average roughness (Sa) of horny layer cells after having added potassium 4-methoxysalicylate (4-MSK) while changing the concentration thereof.

The rates of change of arithmetic average roughness (Sa) of horny layer cells before and after addition of the candidate samples are indicated in FIG. 8. Potassium 4-methoxysalicylate induced a dose-dependent increase in the rate of decrease of arithmetic average roughness (Sa) up to 3.0% by weight, thereby indicating smoothening of the surface of the horny layer cells. As a result, specular reflectance can be expected to improve. Furthermore, since potassium 4-methoxysalicylate is a compound having whitening effects, it is able to act as a skin glow improver by increasing both translucence and specular reflectance.

[Sample Preparation 2]

Candidate samples of trimethylglycine (TMG) were prepared at concentrations of 0% by weight, 5% by weight and 10% by weight.

The rates of change of arithmetic average roughness (Sa) of horny layer cells before and after addition of the candidate samples are indicated in FIG. 9. There were no differences in the rates of decrease of arithmetic average roughness (Sa) at any of the concentrations of trimethylglycine.

[Sample Preparation 3]

Candidate samples containing potassium 4-methoxysalicylate at a concentration of 1.0% by weight and trimethylglycine (TMG) at a concentration of 1% by weight, potassium 4-methoxysalicylate at a concentration of 1.0% by weight and trimethylglycine (TMG) at a concentration of 3% by weight, and potassium 4-methoxysalicylate at a concentration of 1.0% by weight and trimethylglycine (TMG) at a concentration of 5% by weight were prepared in addition to the candidate samples described in the aforementioned Sample Preparation 1.

The rates of change of arithmetic average roughness (Sa) of horny layer cells before and after addition of the candidate samples are indicated in FIG. 10. In the case of having further added TMG, the rate of decrease of Sa increased dose-dependently in comparison with the case of potassium 4-methoxysalicylate at a concentration of 10% by weight. Although trimethylglycine alone did not have an effect on the rate of decrease of Sa, when combined with potassium 4-methoxysalicylate, the rate of decrease of Sa increased significantly, and this can be said to be the result of a synergistic effect.

[Preparation of Sample 1-1]

Potassium 4-methoxysalicylate at 3% by weight and water at 97% by weight were mixed to obtain Sample 1-1.

[Preparation of Sample 1-2]

Potassium 4-methoxysalicylate at 10% by weight and water at 90% by weight were mixed to obtain Sample 1-2.

Figure 11:
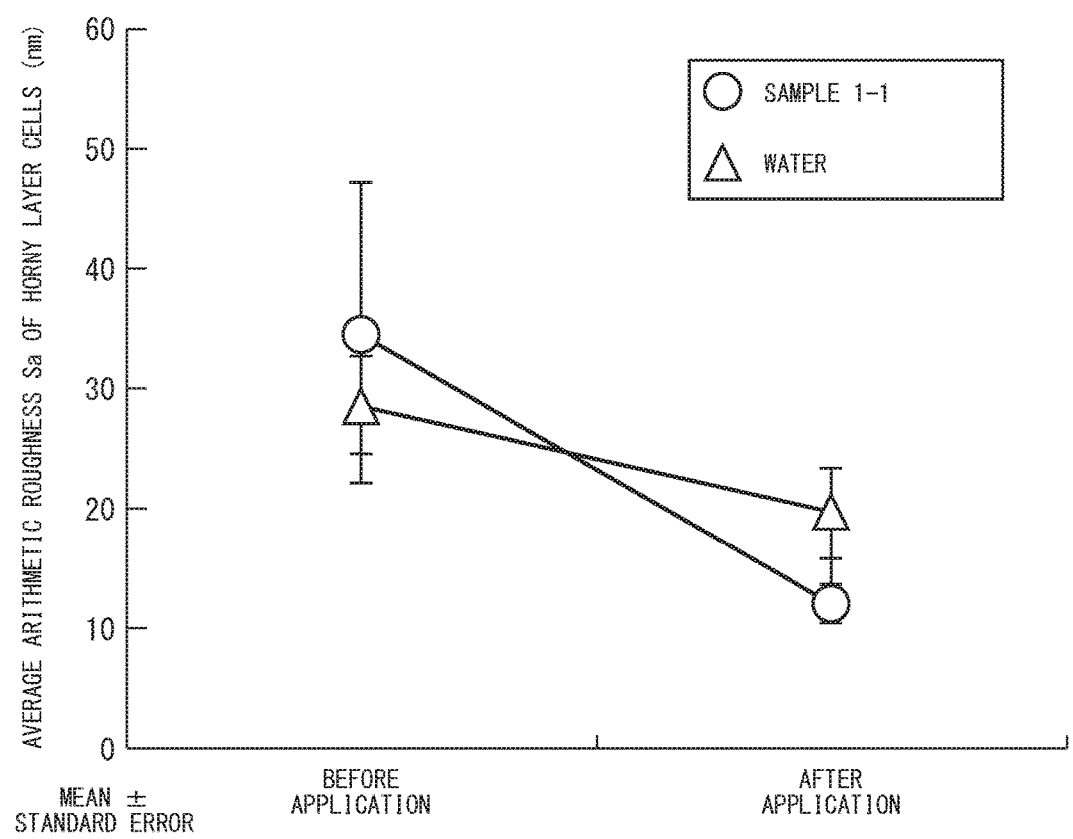
FIG. 11 is a graph indicating arithmetic average roughness (Sa) of horny layer cells before and after applying Sample 1-1 and water.

FIG. 11 indicates arithmetic average roughness (Sa) of horny layer cells before and after application of Sample 1-1. FIG. 11 also indicates the arithmetic average roughness (Sa) of horny layer cells before and after application of water.

Figure 12:
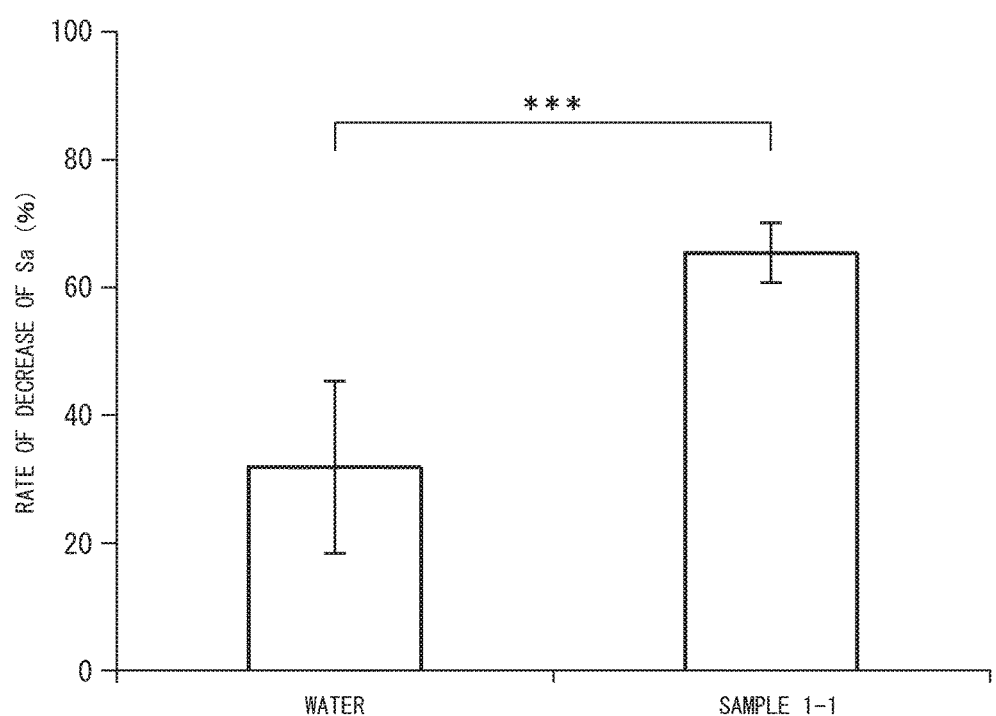
FIG. 12 is a graph indicating the rate of decrease of arithmetic average roughness (Sa) of horny layer cells before and after applying Sample 1-1 and water.

FIG. 12 indicates the rate of decrease of arithmetic average roughness (Sa) of horny layer cells before and after application of Sample 1-1. Here, FIG. 12 also indicates the rate of decrease of arithmetic average roughness (Sa) of horny layer cells before and after application of water.

Based on FIG. 12, Sample 1-1 causes a significant decrease in the arithmetic average roughness (Sa) of horny layer cells in comparison with water, and is able to improve the specular reflectance of skin as a result thereof.

Figure 13:
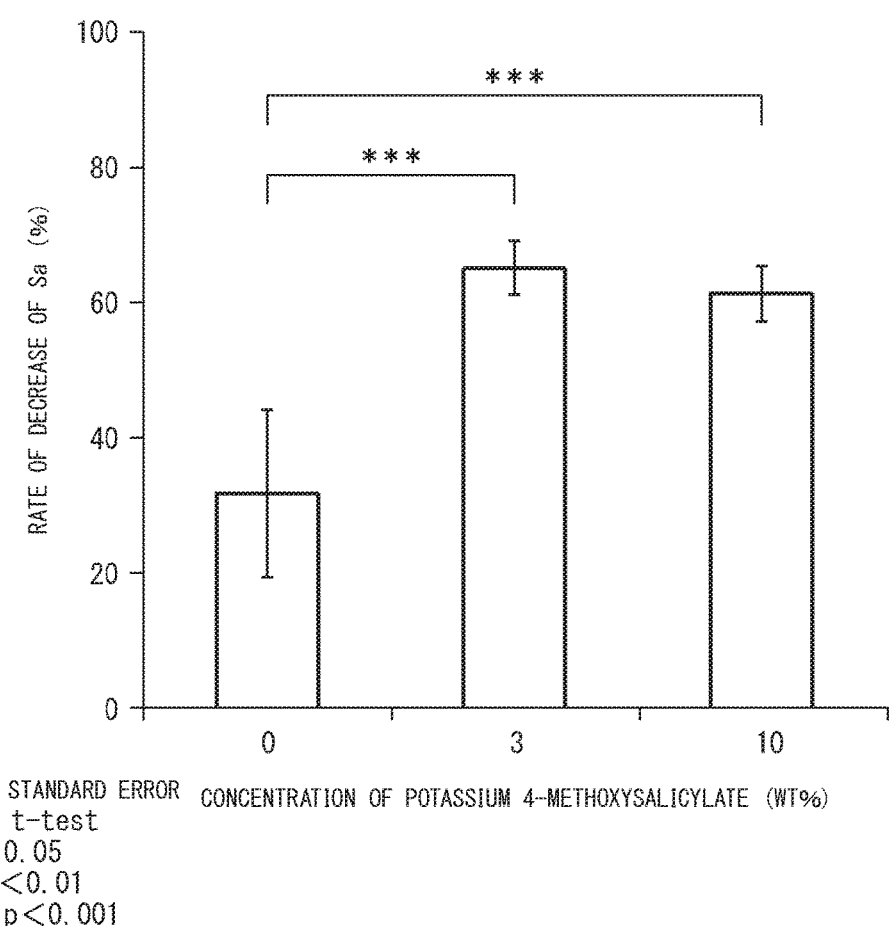
FIG. 13 is a graph indicating the rate of decrease of arithmetic average roughness (Sa) of horny layer cells before and after applying Sample 1-1 and Sample 1-2.

FIG. 13 indicates the rate of decrease of arithmetic average roughness (Sa) of horny layer cells before and after application of Samples 1-1 and 1-2. Here, FIG. 13 also indicates the rate of decrease of arithmetic average roughness (Sa) of horny layer cells before and after application of water.

It can be understood from FIG. 13 that the arithmetic average roughness (Sa) of horny layer cells decreases significantly if the concentration of potassium 4-methoxysalicylate in a sample is 3% by weight to 10% by weight.

[Preparation of Sample 2]

Potassium 4-methoxysalicylate at 1% by weight, trimethylglycine at 5% by weight and water at 94% by weight were mixed to obtain Sample 2.

Figure 14:
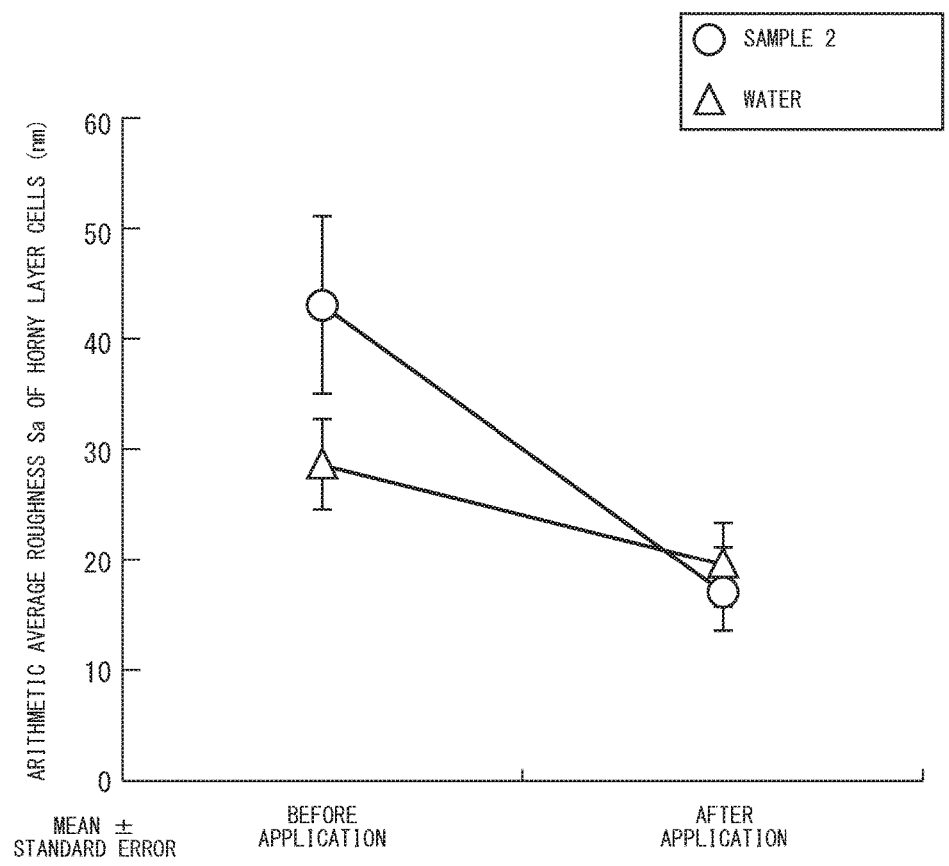
FIG. 14 is a graph indicating arithmetic average roughness (Sa) of horny layer cells before and after applying Sample 2.

FIG. 14 indicates the arithmetic average roughness (Sa) of horny layer cells before and after application of Sample 2. Here, FIG. 14 also indicates the arithmetic average roughness (Sa) of horny layer cells before and after application of water.

Figure 15:
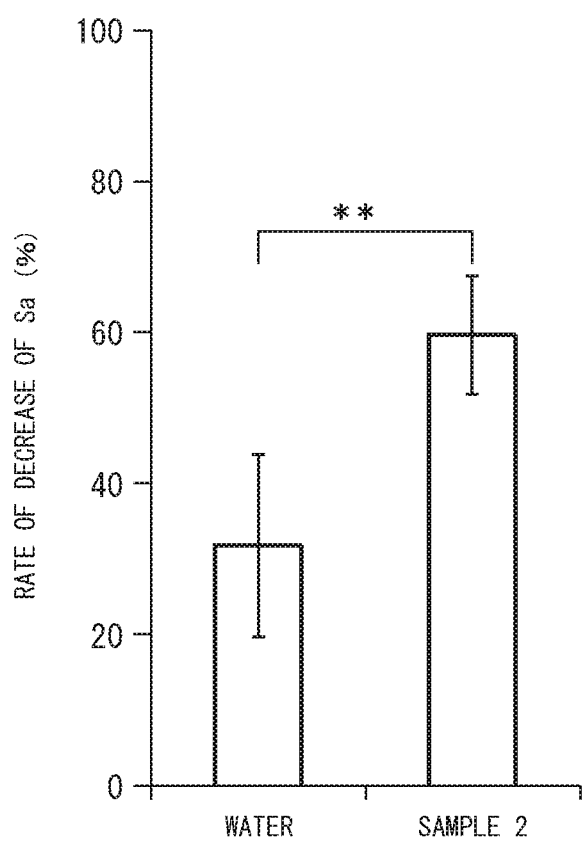
FIG. 15 is a graph indicating the rate of decrease of arithmetic average roughness (Sa) of horny layer cells before and after applying Sample 2 and water.

FIG. 15 indicates the rate of decrease of arithmetic average roughness (Sa) of horny layer cells before and after application of Sample 2. Here, FIG. 15 also indicates the rate of decrease of arithmetic average roughness (Sa) of horny layer cells before and after application of water.

Based on FIG. 15, Sample 2 is able to significantly decrease the arithmetic average roughness (Sa) of horny layer cells in comparison with water, and is able to improve the specular reflectance of skin as a result thereof. Furthermore, specular reflectance of the skin was confirmed to not be improved by trimethylglycine alone.

[Preparation of Sample 3]

Sodium salicylate at 3% by weight and water at 97% by weight were mixed to obtain Sample 3.

Figure 16:
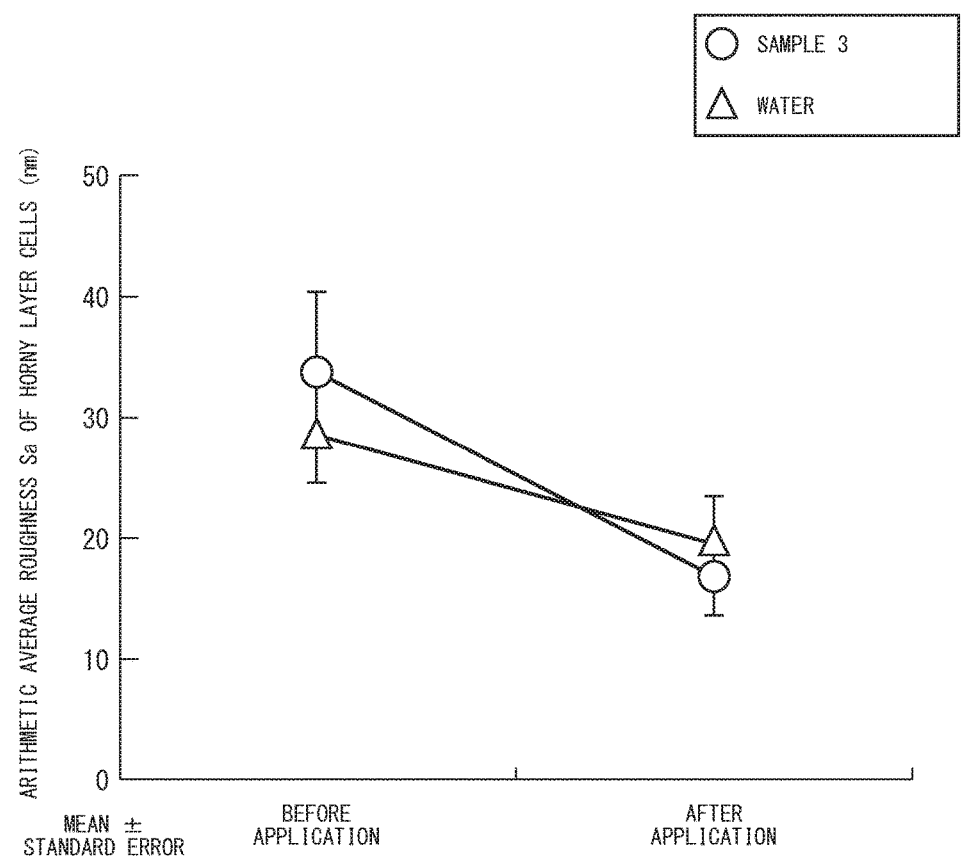
FIG. 16 is a graph indicating arithmetic average roughness (Sa) of horny layer cells before and after applying Sample 3.

FIG. 16 indicates the arithmetic average roughness (Sa) of horny layer cells before and after application of Sample 3. Here, FIG. 16 also indicates the arithmetic average roughness (Sa) of horny layer cells before and after application of water.

Figure 17:
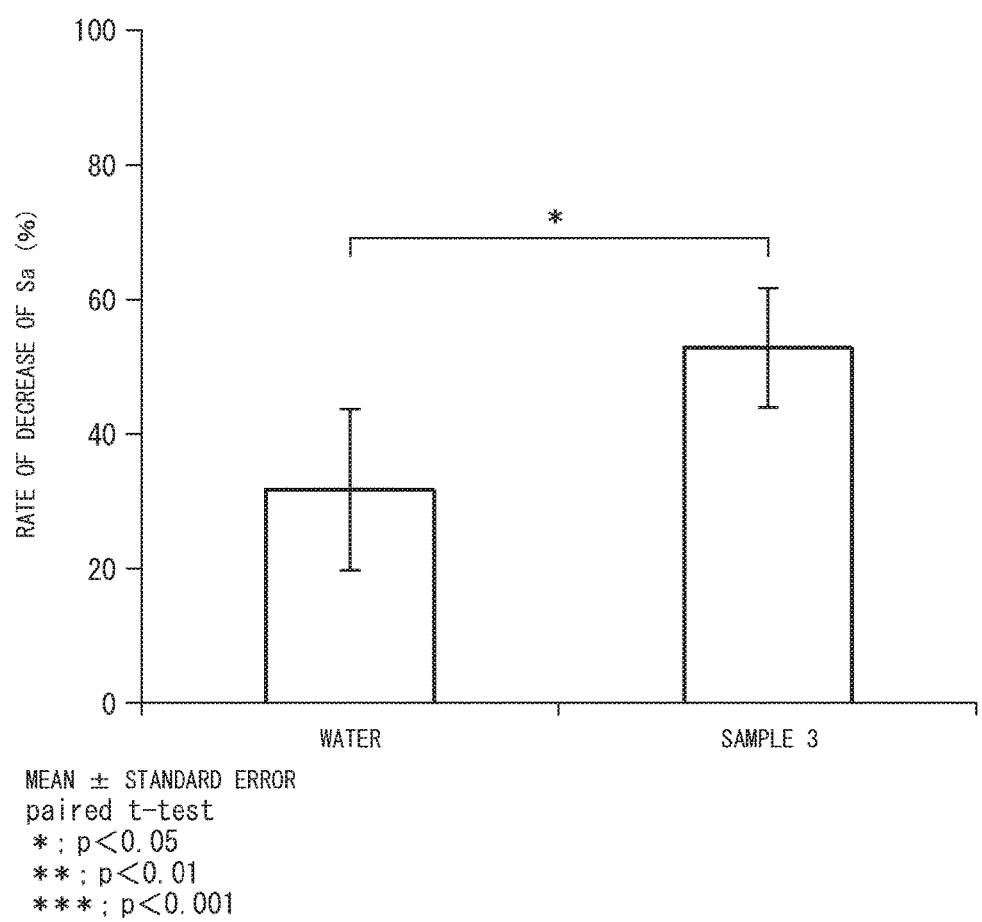
FIG. 17 is a graph indicating the rate of decrease of arithmetic average roughness (Sa) of horny layer cells before and after applying Sample 3 and water.

FIG. 17 indicates the rate of decrease of arithmetic average roughness (Sa) of horny layer cells before and after application of Sample 3. Here, FIG. 17 also indicates the rate of decrease of arithmetic average roughness (Sa) of horny layer cells before and after application of water.

Based on FIG. 17, Sample 3 is able to significantly decrease the arithmetic average roughness (Sa) of horny layer cells in comparison with water, and is able to improve the specular reflectance of skin as a result thereof.

[Preparation of Sample 4-1]

Glycolic acid at 4% by weight and water at 96% by weight were mixed to obtain Sample 4-1.

[Preparation of Sample 4-2]

Glycolic acid at 40% by weight and water at 60% by weight were mixed to obtain Sample 4-2.

Figure 18:
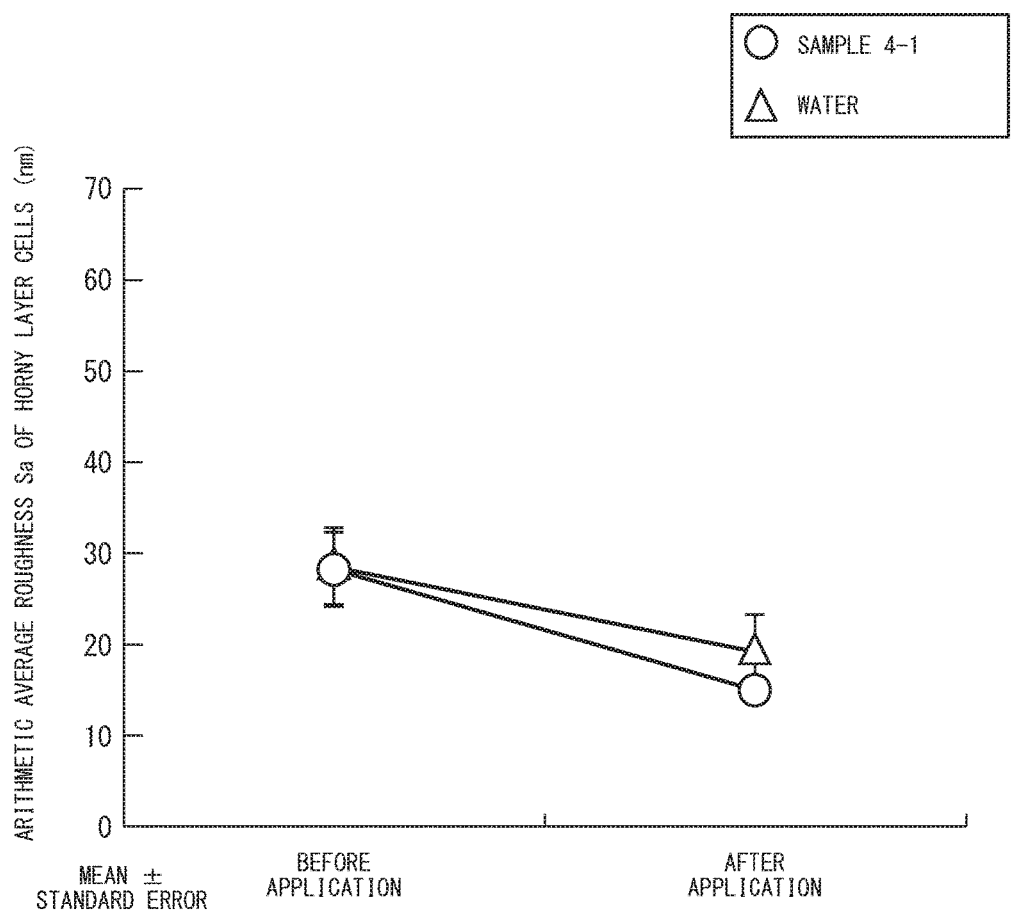
FIG. 18 is a graph indicating arithmetic average roughness (Sa) of horny layer cells before and after applying Sample 4-1.

FIG. 18 indicates the arithmetic average roughness (Sa) of horny layer cells before and after application of Sample 4-1. Here, FIG. 18 also indicates the arithmetic average roughness (Sa) of horny layer cells before and after application of water.

Figure 19:
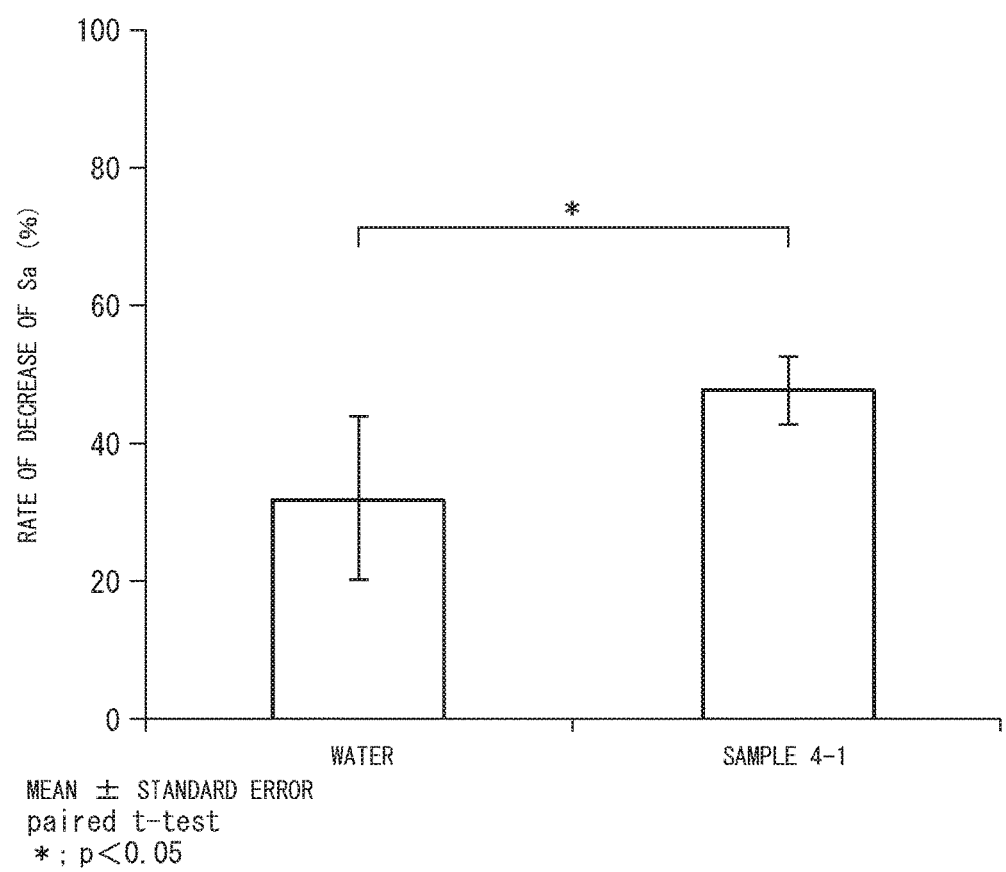
FIG. 19 is a graph indicating the rate of decrease of arithmetic average roughness (Sa) of horny layer cells before and after applying Sample 4-1 and water.

FIG. 19 indicates the rate of decrease of arithmetic average roughness (Sa) of horny layer cells before and after application of Sample 4-1. Here, FIG. 19 also indicates the rate of decrease of arithmetic average roughness (Sa) of horny layer cells before and after application of water.

Based on FIG. 19, Sample 4-1 is able to significantly decrease the arithmetic average roughness (Sa) of horny layer cells in comparison with water, and is able to improve the specular reflectance of skin as a result thereof.

Figure 20:
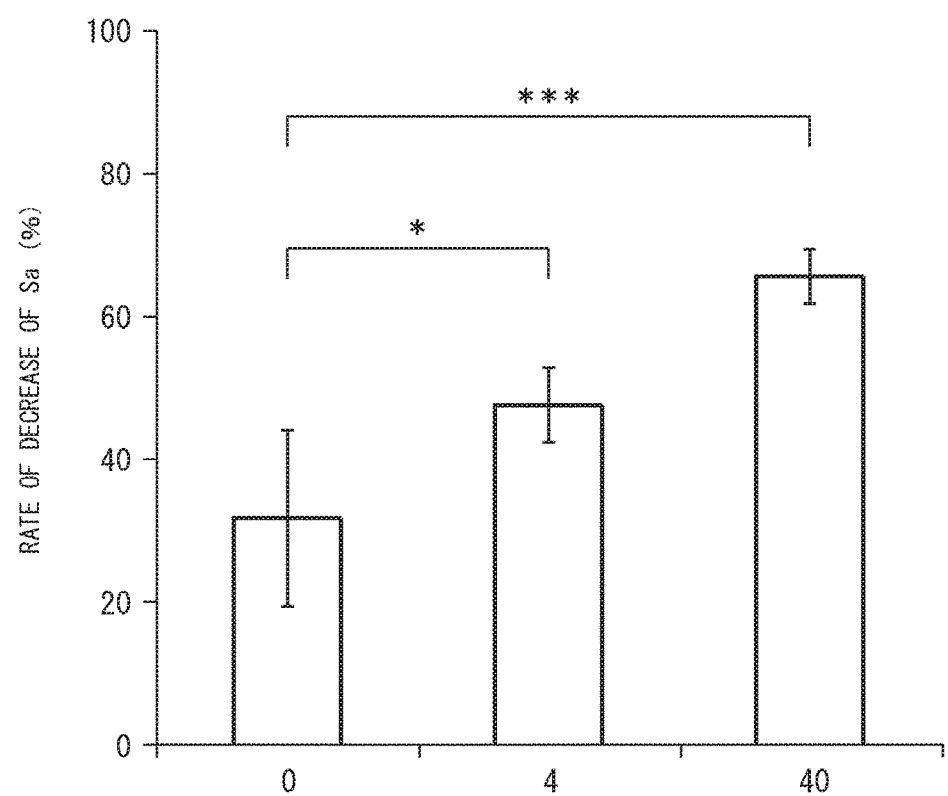
FIG. 20 is a graph indicating arithmetic average roughness (Sa) of horny layer cells before and after applying Sample 4-1 and Sample 4-2.

FIG. 20 indicates the rate of decrease of arithmetic average roughness (Sa) of horny layer cells before and after application of Samples 4-1 and 4-2. Here, FIG. 20 also indicates the rate of decrease of arithmetic average roughness (Sa) of horny layer cells before and after application of water.

It can be understood from FIG. 20 that the arithmetic average roughness (Sa) of horny layer cells decreases significantly if the concentration of glycolic acid in an external skin preparation is 4% by weight to 40% by weight.

[Preparation of Sample 5]

Glycolic acid at 2% by weight, trimethylglycine at 5% by weight and water at 93% by weight were mixed to obtain Sample 5.

Figure 21:
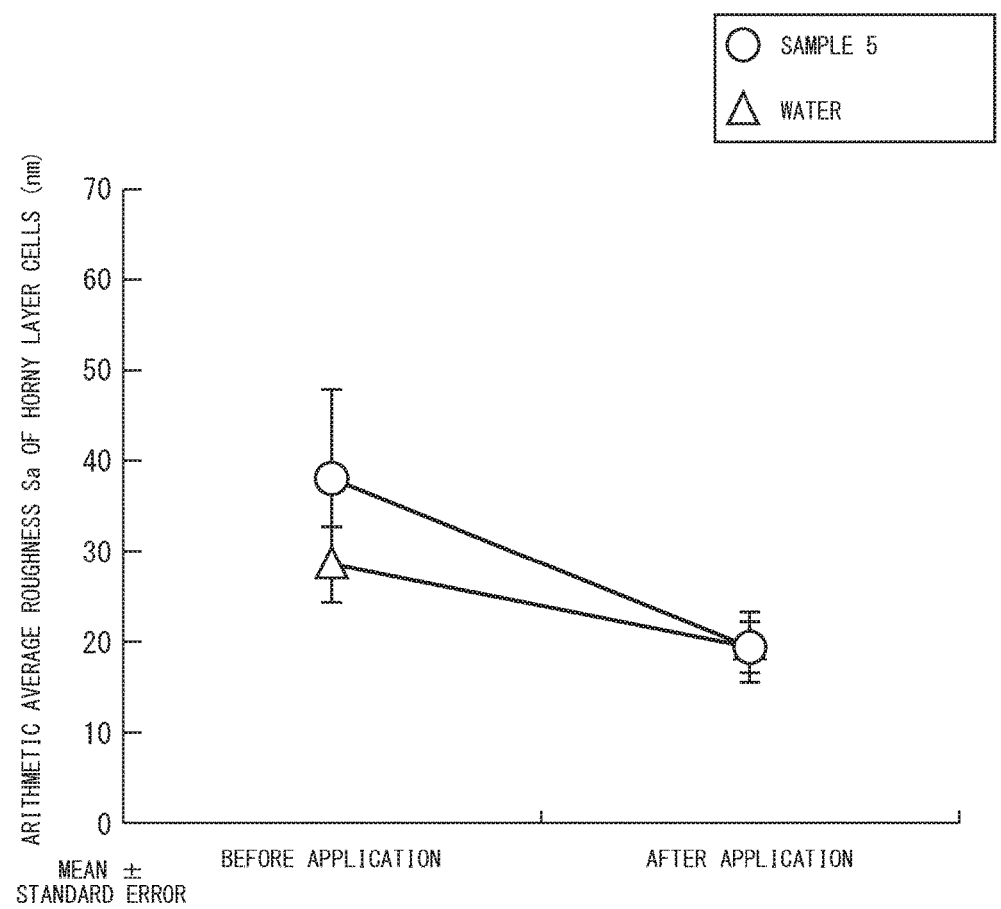
FIG. 21 is a graph indicating arithmetic average roughness (Sa) of horny layer cells before and after applying Sample 5.

FIG. 21 indicates the arithmetic average roughness (Sa) of horny layer cells before and after application of Sample 5. Here, FIG. 21 also indicates the arithmetic average roughness (Sa) of horny layer cells before and after application of water.

Figure 22:
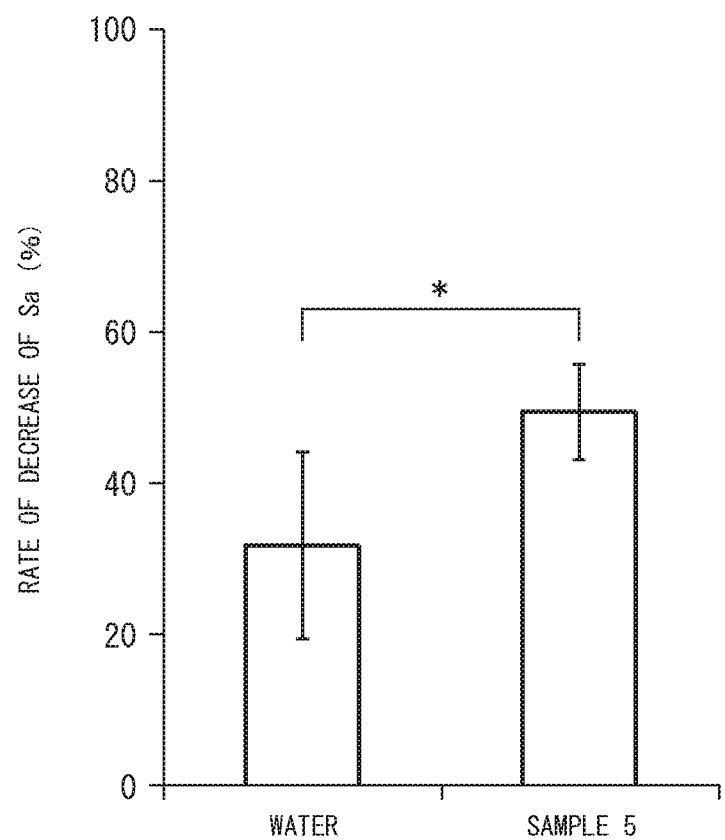
FIG. 22 is a graph indicating the rate of decrease of arithmetic average roughness (Sa) of horny layer cells before and after applying Sample 5 and water.

FIG. 22 indicates the rate of decrease of arithmetic average roughness (Sa) of horny layer cells before and after application of Sample 5. Here, FIG. 22 also indicates the rate of decrease of arithmetic average roughness (Sa) of horny layer cells before and after application of water.

Based on FIG. 22, Sample 5 is able to significantly decrease the arithmetic average roughness (Sa) of horny layer cells in comparison with water, and is able to improve the specular reflectance of skin as a result thereof.

[Example 6] Skin Application Test

Female subjects aged 31 to 59 years were divided into three groups and candidate skin lotiones were applied to their cheeks for 3 months once a day after bathing. The subjects were given questionnaires at one month, two months and three months after the start of application. In addition, horny layer samples were simultaneously acquired from the subjects and used to measure skin grain and horny layer roughness. Specular reflectance and diffuse reflectance were measured using Samba Face to evaluate skin glow.

[Candidate Skin Lotiones]

The skin lotiones indicated below were used in testing.

A: Milky skin lotion not incorporating medicinal agent (control group)

B: Milky skin lotion incorporating 1% potassium 4-methoxysalicylate and 5% trimethylglycine (1% 4-MSK+5% TMG group)

C: Milky skin lotion incorporating 3% potassium 4-methoxysalicylate (3% 4-MSK group)

The skin lotion indicated below was used for the milky skin lotion.

| (Incorporated Components) | (wt %) |
|---|---|
| Ethanol | 5% |
| Glycerin | 2% |
| Dipropylene glycol | 4% |
| 1,3-butylene glycol | 2% |
| Xanthan gum | 0.1% |
| Polyoxyethylene glyceryl isostearate | 1% |
| Lipophilic glyceryl monostearate | 2% |
| Batyl alcohol | 1% |
| Behenyl alcohol | 2.5% |
| Methyl polysiloxane | 5% |
| Hydrogenated oil | 2.5% |
| Jojoba oil | 3% |
| Cetyl ethylhexanoate | 3% |
| Citric acid | As suitable |
| Sodium citrate | As suitable |
| EDTA-3Na | As suitable |
| Methyl p-hydroxybenzoate | As suitable |
| Water | Balance |
|  | 100% |

[Questionnaire]

Figure 23:
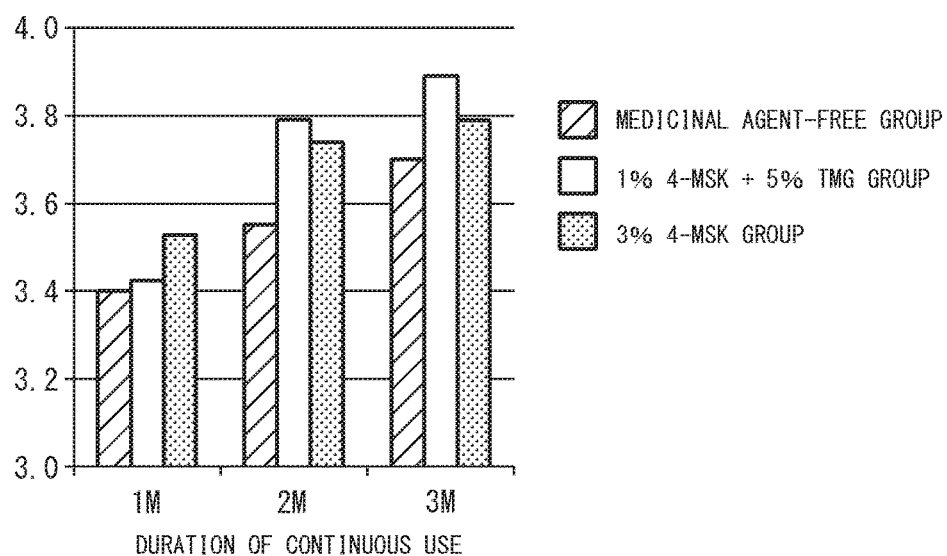
FIG. 23 indicates the results of a questionnaire given after continuous use of candidate skin lotiones.

The contents of the questionnaire consisted of ranking improvement of skin glow by assigning a value of 5 points for improved, 4 points for somewhat improved, 3 points for no change, 2 points for somewhat worsened and 1 point for worsened followed by calculating the average scores. The results obtained in the 1st month, 2nd month and 3rd month are shown in FIG. 23.

[Measurement of Horny Layer Roughness]

Figure 24:
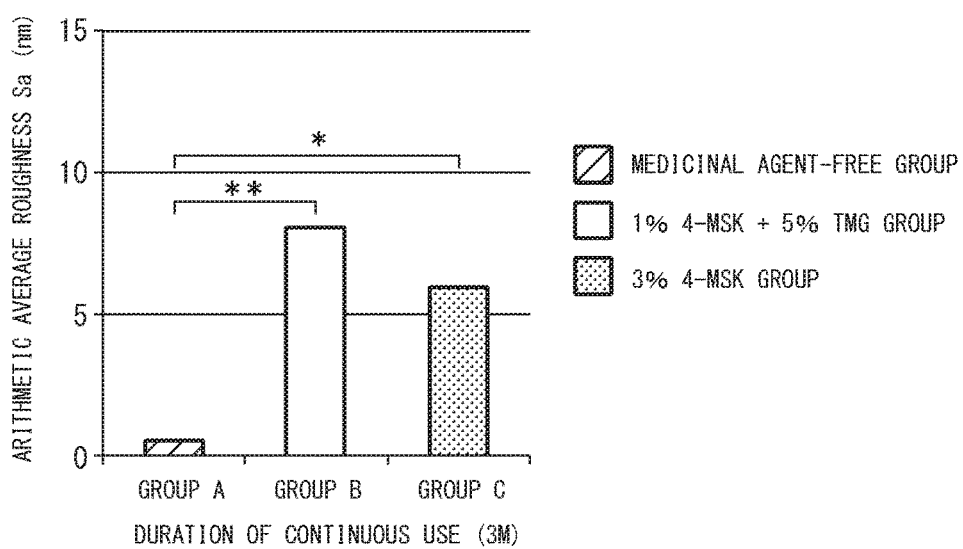
FIG. 24 indicates the rate of decrease of arithmetic average roughness (Sa) of horny layer cells in the third month of continuous use of candidate skin lotiones.

Samples of the corny layer were exfoliated from the surface of subjects' skin using adhesive strips (Post-It®, 3M Corp.). Arithmetic average roughness (Sa) was measured in accordance with the method described in Example 4 followed by determination of the average value thereof, and results for the rate of decrease in comparison with arithmetic average roughness (Sa) prior to application are shown in FIG. 24.

[Measurement of Skin Texture]

Figure 25:
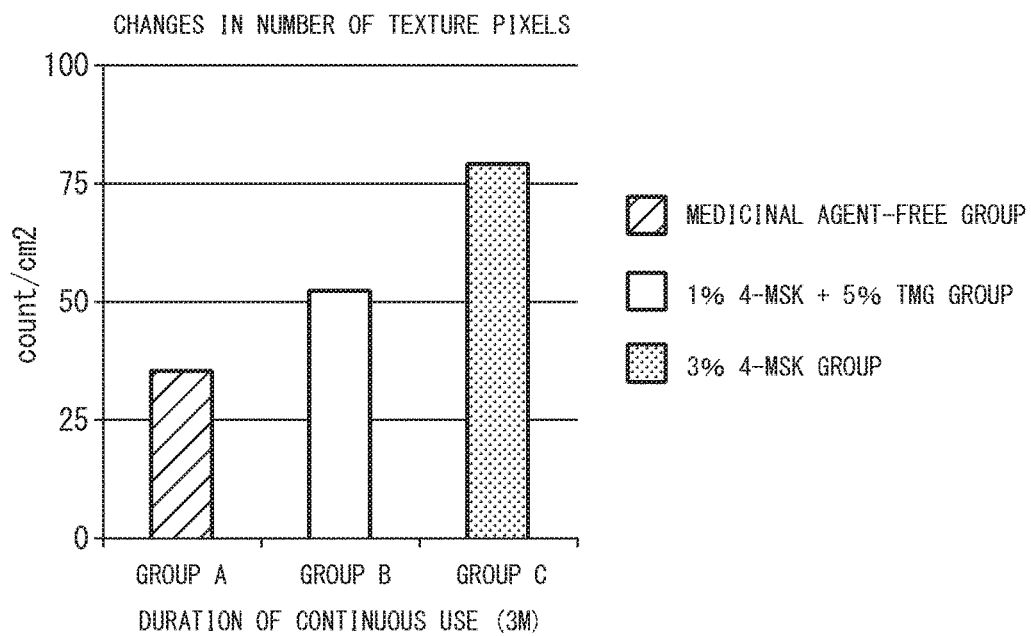
FIG. 25 indicates changes in the number of texture pixels in the third month of continuous use of candidate skin lotiones.

Samples of the corny layer were exfoliated from the surface of subjects' skin using adhesive strips (Post-It®, 3M Corp.). The exfoliated horny layer cells were transferred to carbon conductive adhesive tape adhered to the stand of a scanning electron microscope (SEM) followed by observation of the cells by SEM. The number of texture pixels was measured using image processing (see Skin Res. Technol., 2014, 20: 299-306). The results are shown in FIG. 25.

[Evaluation of Glow]

Figure 26:
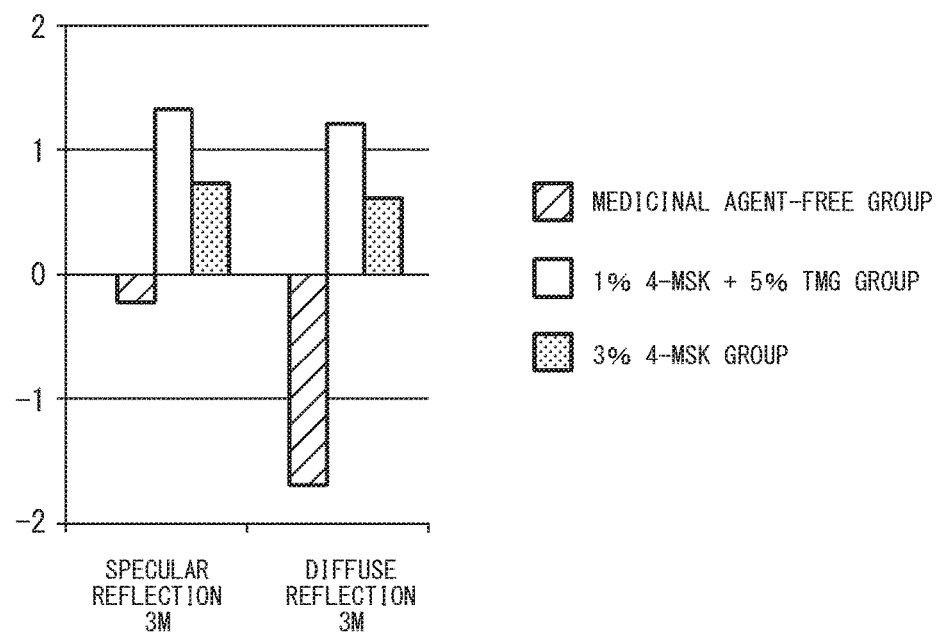
FIG. 26 indicates changes specular reflectance and diffuse reflectance in the third month of continuous use of candidate skin lotiones.

Specular reflectance and diffuse reflectance of subjects were measured using the method described in Example 1. The results for specular reflectance and diffuse reflectance three months later versus specular reflectance and diffuse reflectance prior to application are shown in FIG. 26.

Improvement of skin glow was observed in both the 1% 4-MSK+5% TMG group and 3% 4-MSK group for both the results of the questionnaire and the glow evaluation results, and the degree of improvement was indicated to be superior in the 1% 4-MSK+5% TMG group. In addition, a similar trend was observed in the evaluation of glow based on horny layer roughness. Moreover, results indicating that skin texture was finer were obtained in both the 1% 4-MSK+5% TMG group and 3% 4-MSK group based on the results of measuring skin texture. Although specular reflectance is known to increase as skin texture becomes coarser, the 1% 4-MSK+5% TMG and 3% 4-MSK groups each indicated that specular reflectance can be increased without making skin texture coarser.

The invention claimed is:

1. A method for evaluating a glow of a skin, comprising:
   measuring a first reflectance by irradiating polarized light to a surface of the skin followed by receiving reflected light polarized in a direction parallel to the direction of polarization of the irradiated polarized light,
   measuring a second reflectance by irradiating the polarized light to the surface of the skin followed by receiving reflected light in a direction perpendicular to the direction of polarization of the irradiated polarized light, and
   determining diffuse reflectance and specular reflectance from the first reflectance and the second reflectance;
   wherein the skin is determined to have the glow in the case when the determined diffuse reflectance is 25% or more and the determined specular reflectance is 10% or more.

2. The method for evaluating skin glow according to claim 1, further comprising applying a test sample to the skin before measuring the first reflectance and the second reflectance.

3. The method of claim 1, wherein the skin is determined to have the glow when determined diffuse reflectance is 27% or more and the determined specular reflectance is 12% or more.

4. The method of claim 3, wherein the diffuse reflectance is determined by doubling the first reflectance and the specular reflectance is determined by subtracting the second reflectance from the first reflectance.

5. The method of claim 1, wherein the diffuse reflectance is determined by doubling the first reflectance and the specular reflectance is determined by subtracting the second reflectance from the first reflectance.

* * * * *